US 8,637,521 B2

(12) United States Patent
Deigin

(10) Patent No.: US 8,637,521 B2
(45) Date of Patent: Jan. 28, 2014

(54) SUBSTITUTED PIPERAZIN-2,5-DIONES AND THEIR USE AS MULTIFUNCTIONAL BIOACTIVE COMPOUNDS

(75) Inventor: Vladislav I. Deigin, Richmond Hill (CA)

(73) Assignee: Manus Pharmaceuticals (Canada) Ltd., Toronto (CA)

( * ) Notice: Subject to any disclaimer, the term of this patent is extended or adjusted under 35 U.S.C. 154(b) by 168 days.

(21) Appl. No.: 12/376,138

(22) PCT Filed: Aug. 1, 2007

(86) PCT No.: PCT/CA2007/001357
§ 371 (c)(1),
(2), (4) Date: Oct. 22, 2009

(87) PCT Pub. No.: WO2008/014613
PCT Pub. Date: Feb. 7, 2008

(65) Prior Publication Data
US 2010/0048586 A1    Feb. 25, 2010

Related U.S. Application Data

(60) Provisional application No. 60/835,428, filed on Aug. 4, 2006.

(51) Int. Cl.
*A61K 31/4965* (2006.01)
(52) U.S. Cl.
USPC .................. 514/255.02; 544/385; 548/469
(58) Field of Classification Search
USPC .................. 514/255.02; 544/385; 548/469
See application file for complete search history.

(56) References Cited

U.S. PATENT DOCUMENTS

| 4,006,261 | A | * | 2/1977 | Pickenhagen et al. ........ 426/537 |
| 4,331,595 | A | | 5/1982 | Heavner et al. |
| 5,932,579 | A | | 8/1999 | Campbell et al. |
| 5,976,569 | A | | 11/1999 | Milstein |
| 6,060,452 | A | | 5/2000 | Green et al. |
| 6,103,699 | A | | 8/2000 | Deigin et al. |
| 2003/0171379 | A1 | | 9/2003 | Jacobs et al. |
| 2004/0102454 | A1 | | 5/2004 | Hayashi et al. |

FOREIGN PATENT DOCUMENTS

| CA | 1257265 | | 7/1989 |
| CA | 2417960 | | 2/2002 |
| CA | 2523467 | | 12/2004 |
| DE | 19937721 | A1 | 8/1999 |
| EP | 0388750 | A1 | 9/1990 |
| EP | 0517589 | A2 | 9/1992 |
| FR | 2722787 | A1 | 1/1996 |
| JP | 10226615 | A | 8/1998 |
| JP | 2001247566 | A | 9/2001 |
| WO | 9308815 | A1 | 5/1993 |
| WO | 2004103304 | A2 | 12/2004 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
International Search Report for PCT Application No. PCT/CA2007/001357, completed on Oct. 30, 2007.
Mihala, N. et al., "The synthesis of alternative diketopiperazines as potential RGD mimetics" Journal of Peptide Science, 2006: 12: 663-669.
Bergerton, R. J. et al., "An Investigation of the Impact of Molecular Geometry upon Microcapsule Self-Assembly" J. Am. Chem. Soc 1995, 117, 6658-6665.
Bergeron, R. J. et al., "Macromolecular Self-Assembly of Diketopiperazine Tetrapeptides", J .Am. Chem. Soc. 1994, 116, 8479-8484.
Schon, I et al., "Formation of Aminosuccinyl Peptides During Acidolytic Deprotection Followed by their Transformation of Piperazine-2,5-Dione Derivatives in Neutral Media", Int. J. Peptide Protein Res. 14, 1979, 485-494.
Schaschke, N. et al., "Bivalent Inhibition of β-Tryptase: Distance Scan of Neighboring Subunits by Dibasic Inhibitors", Bioorganic and Medicinal Chemistry Letters 12, 2002, 985-988.
Semina, O. V. et al., "Effects of Structural and "Mixed" Isomers of Glu-Trp Dipedptide on Normal Hemopoietic Stem Cells", Bulletin of Experimental Biology and Medicine, vol. 141, No. 2, Feb. 2006, 250-253.
Eurasian Patent Application No. 200970178, Office Action dated Oct. 19, 2010.
European Patent Application No. 07785022.0, Extended Search Report dated Aug. 6, 2010.

* cited by examiner

*Primary Examiner* — Douglas M Willis
(74) *Attorney, Agent, or Firm* — Bereskin & Parr LLP/S.E.N.C.R.L., s.r.l.; Patricia Folkins

(57) ABSTRACT

The present invention discloses multifunctional bioactive compounds of formula (I) constituted of an immunoregulatory portion linked to a stabilizer moiety and pharmaceutical compositions thereof useful in the treatment of immune disorders and hemopoietic disorders such as immune cytopema, multiple myeloma, chronic lymphoid leucosis, lymphocytic lymphomas, lymphosarcomas.

18 Claims, 4 Drawing Sheets

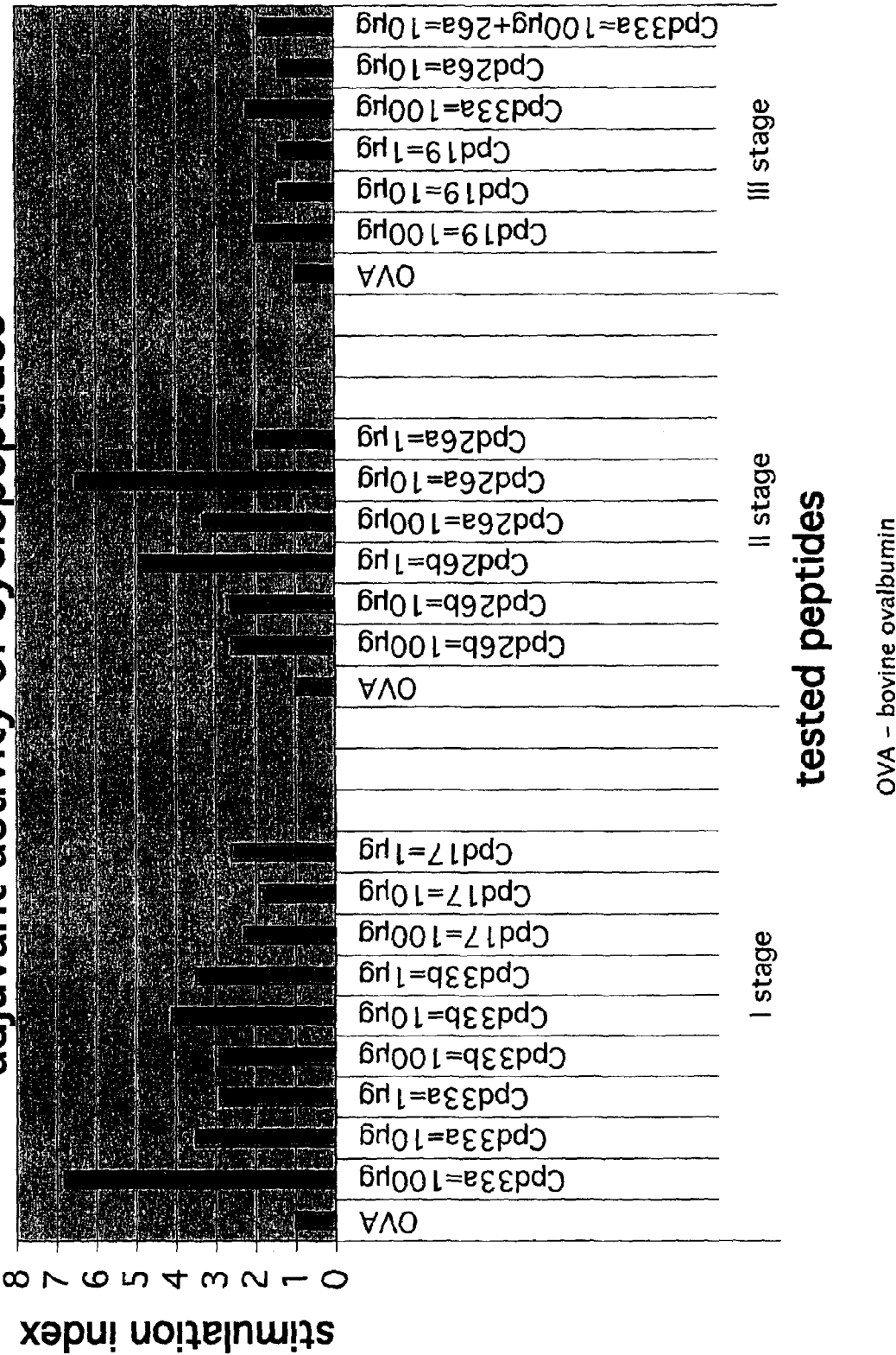

SUBSTITUTED PIPERAZIN-2,5-DIONES AND THEIR USE AS MULTIFUNCTIONAL BIOACTIVE COMPOUNDS

FIELD OF THE INVENTION

The present invention relates to compounds, compositions, methods, and applications of a novel approach to administer bioactive compounds to patients in need thereof.

BACKGROUND OF THE INVENTION

Radiotherapy and chemotherapy are well-established treatment methods for malignant diseases. Cells, which grow and divide rapidly, are most vulnerable to the effects of radiation and cytotoxic agents. Among those effected are tumor cells, and normal cells including hair and intestinal cells, and cells of the hemopoietic and immune systems. Damage to normal cells of the hemopoietic and immune systems by radiation and cytotoxic agents often has life-threatening consequences, and it limits the ability to administer a full therapeutic dose.

There has been extensive research to identify agents which will protect normal hemopoietic and immunologic cells from the effects of radiotherapy and chemotherapy, or aid in the reconstitution of cells suppressed by these therapies. For example, transforming growth factor beta-1 has been reported to be useful for protecting hematopoietic stem cells from the myelotoxicity of chemotherapeutic drugs or radiation therapy (U.S. Pat. No. 5,278,145 to Keller et al.). A lyophilized composition containing human albumin in thymosin alpha 1 was also reported to exert a preventative activity against progression of leukemia in mice whose immune systems were severely damaged by treatment with cytostatic agents or radiation treatment. Hemopoietic growth factors such as interleukin-3 and CSF have been used to potentiate immune response or assist in reconstituting normal blood following radiation- or -chemotherapy-induced hematopoietic cell suppression (WO 88/05469 to Anderson et al., U.S. Pat. No. 4,959,455 to Ciarletta et al; U.S. Pat. No. 4,999,291 to Souza).

Semina et al. (Radiatsionnaya Biologiya Radioekologiya 33(3), 1993; WO 89/06134) have shown that the levorotary (L) enantiomer of the dipeptide H-Glu-Trp-OH acts as an immunostimulant and can induce the proliferation of cells. As such, these dipeptides are useful in reconstituting hemopoietic and immune cells after chemotherapy or irradiation therapy.

Several peptides with immunoregulatory properties have been synthesized (for example, SU 1,582,393; EP 230,052; U.S. Pat. No. 4,190,646; U.S. Pat. No. 5,008,246; and U.S. Pat. No. 5,013,723). Many scientific laboratories have tried to develop methods for preparing synthetic derivatives of natural peptides, which are more active than their natural analogs (for example, EP 136,720; and EP 137,904).

Australian Patent No. AU-B-29308/89 (corresponding to WO 089/06134) teaches the preparation of Glu-Trp and its use for treating immune deficiency conditions. WO 93/08815 issued to Khavinson et al. discloses the peptide Glu-Trp and cyclic monomers and polymers thereof, for use in the treatment of immunosuppression.

Deigin et al., U.S. Pat. No. 6,051,683, issued Apr. 18, 2000 and U.S. Pat. No. 6,159,940 issued Dec. 12, 2002, describe immunoregulatory peptides of the general formula:

X-Glu-Trp-Y that can stimulate the immune response and modulate hemopoiesis;
wherein X is hydrogen, glycine, alanine, leucine, isoleucine, valine, N-valine, proline, tyrosine, phenylalanine, tryptophan, D-alanine, D-leucine, D-isoleucine, D-valine, D-N-valine, D-proline, D-tyrosine, D-phenylalanine, D-tryptophan, γ-aminobutyric acid or ξ-aminocaproic acid; Y is glycine, alanine, leucine, isoleucine, valine, N-valine, proline, tyrosine, phenylalanine, tryptophan, D-alanine, D-leucine, D-isoleucine, D-valine, D-N-valine, D-proline, D-tyrosine, D-phenylalanine, D-tryptophan, γ-aminobutyric acid, ξ-aminocaproic acid, —OH, $NH_2$, $N_2H_3$, or a mono- or di-substituted amide (C1-C3); and more particularly H-Ile-Glu-Trp-OH.

Deigin et al., U.S. Pat. No. 5,736,519 issued Apr. 7, 1998; U.S. Pat. No. 6,103,699 issued Aug. 15, 2000 and U.S. Pat. No. 6,410,515 issued Jun. 25, 2003 describe immunoregulatory peptides of the general formula:

X-A-D-Trp-Y for reconstitution of cells after radiation or chemotherapy, for inhibiting cell proliferation, and for immunosuppression, wherein X is hydrogen, glycine, alanine, leucine, isoleucine, valine, N-valine, proline, tyrosine, phenylalanine, tryptophan, D-alanine, D-leucine, D-isoleucine, D-valine, D-N-valine, D-proline, D-tyrosine, D-phenylalanine, D-tryptophan, γ-aminobutyric acid or ξ-aminocaproic acid; A is D-glutamic acid or D-γ-glutamic acid; and Y is glycine, alanine, leucine, isoleucine, valine, N-valine, proline, tyrosine, phenylalanine, tryptophan, D-alanine, D-leucine, D-isoleucine, D-valine, D-N-valine, D-proline, D-tyrosine, D-phenylalanine, D-tryptophn, γ-aminobutyric acid, ξ-aminocaproic acid, hydroxyl, or an amide group; and more particularly H-γ-DGlu-Trp-OH.

Deigin et al., U.S. Pat. No. 6,184,208, issued Feb. 6, 2001 and U.S. Pat. No. 6,248,716, issued Jun. 19, 2001 describe immunoregulatory peptides of the general formula:

X-Tyr-Y-Phe-Z-A that reduce stress, stimulate weight gain, epithelium growth zone, wound healing and reparative and anabolic processes; wherein X is hydrogen, arginine, D-arginine, ornithine, D-ornithine, lysine, D-lysine, homoarginine, D-homoarginine, citrulline, D-citrulline; Tyr is tyrosine; Y is D-alanine, D-valine, D-leucine, D-isoleucine, D-phenylalanine, D-asparagine, D-tryptophan, D-proline, D-serine, D-threonine, D-tyrosine, D-hydroxyproline, D-cysteine, D-cysteyl-cysteine, D-methionine, D-lysine, D-homoarginine, D-arginine, D-histidine, D-aspartic acid, D-glutamic acid, D-β-alanine, or D-ornithine; Phe is phenylalanine; Z is alanine, D-alanine, valine, D-valine, leucine, D-leucine, isoleucine, D-isoleucine, phenylalanine, D-phenylalanine, asparagine, D-asparagine, glycine, glutamine, D-glutamine, tryptophan, D-tryptophan, proline, D-proline, serine, D-serine, threonine, D-threonine, tyrosine, D-tyrosine, hydroxyproline, D-hydroxyproline, cysteine, D-cysteine, cysteyl-cysteine, cysteine-D-cysteine, D-cysteyl cysteine, D-cysteine-D-cysteine, methionine, D-methionine, lysine, D-lysine, arginine, D-arginine, histidine, D-histidine, aspartic acid, D-aspartic acid, glutamic acid, D-glutamic acid, β-alanine, D-β-alanine, ornithine, or D-ornithine; and, A is hydroxyl or substituted amide (C1-C3); and more particularly H-Arg-Tyr-D-Ala-Phe-Gly-OH.

Compositions for the delivery, in particular, oral delivery, of active agents comprising a diketopiperazine-based system are described in several patents and patent applications owned by Emisphere Technologies, Inc., including for example, U.S. Pat. Nos. 6,663,898, 6,395,774, 6,331,318, 5,976,569 and 5,693,338, as well as U.S. Patent Application Nos. 20030198658, 20030155993 and 20030028250. In these compositions, the diketopiperazine is typically added as a separate component.

There remains a need for effective methods for delivering bioactive compounds to the body that may be readily tailored for any applications or for multiple applications.

SUMMARY OF THE INVENTION

The present invention represents a new platform for the therapeutic delivery of multifunctional bioactive compounds. The invention relates to molecules that possess an immunoregulatory portion linked to a stabilizer moiety. The stabilizer moiety acts as an effective carrier for the immunoregulator into the body. Further, the immunoregulator and stabilizer may be optionally linked to another functionally bioactive molecule. The bioactive molecule possesses either further immunoregulatory activity, activity which complements or synergizes with the immunoregulatory portion or a different therapeutic activity.

Accordingly, the present invention includes a multifunctional bioactive compound selected from one or more of a compound of Formula I:

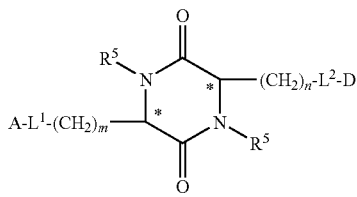

wherein

A is an immunoregulatory radical selected from the group consisting of Trp, Tyr, Phe, His, aryl and heteroaryl, where the aryl and heteroaryl groups may be optionally substituted with 1 to 6 substituents independently selected from the group consisting of halo, OH, $OC_{1-6}$alkoxy, $C_{1-6}$alkyl, $C_{2-6}$alkenyl, $C_{2-6}$alkenyloxy, $NH_2$, $NH(C_{1-6}$alkyl), $N(C_{1-6}$alkyl)($C_{1-6}$alkyl), CN, $CF_3$, $OCF_3$, $NO_2$, $C(O)C_{1-6}$alkyl, $C(O)OC_{1-6}$alkyl, $SO_2C_{1-6}$alkyl, $SO_2NH_2$, $SO_2NHC_{1-6}$alkyl, phenyl and $C_{1-6}$alkylenephenyl, and where heteroaryl is an aromatic carbocyclic ring containing from 5 to 10 carbon atoms, in which 1 to 4 carbon atoms have been replaced with a heteroatom selected from one or more of O, S and N—$R^1$, where $R^1$ is selected from the group consisting of H, $C_{1-6}$alkyl, $C_{1-4}$alkylenearyl, $C(O)C_{1-6}$alkyl, $C(O)$aryl, $SO_2C_{1-6}$alkyl and $SO_2$aryl when the N atom is $sp^3$ hybridized, or is a lone pair of electrons when the N atom is $sp^2$ hybridized;

$L^1$ and $L^2$ are each independently a linker group selected from the group consisting of a single bond, —C(O)——C(O) $NR^2$—, —$NR^2C(O)$—, —$NR^2$—, —C(O)—O—, —OC (O)—, —S—S—, $SO_2NR^2$—, $NR^2SO_2$, —S— and —O—; $R^2$ is selected from the group consisting of H, $C_{1-6}$alkyl, $C_{1-6}$alkylenearyl, $C(O)C_{1-6}$alkyl, $C(O)$aryl, $SO_2C_{1-6}$alkyl and $SO_2$aryl;

$R^5$ is H or $C_{1-6}$alkyl;

* is the L or D configuration or mixtures thereof;

m is an integer between 1 and 50;

n is an integer between 0 and 50; and

D is selected from the group consisting of H, $C_{1-6}$alkyl, any side chain of an amino acid and any functionally active molecule, and pharmaceutically acceptable salts, solvates and prodrugs thereof.

The present invention further relates to pharmaceutical compositions comprising a multifunctional bioactive compound of the invention and a pharmaceutically acceptable carrier.

Also included in the present invention are methods of treating immune disorders, and optionally other disorders in the same subject, comprising administering an effective amount of a multifunctional bioactive compound of the invention to a subject in need thereof. Further, there is provided a use of a multifunctional bioactive compound of the invention to treat immune disorders, and optionally other disorders in the same subject, as well as a use of a multifunctional bioactive compound of the invention to prepare a medicament to treat immune disorders, and optionally other disorders in the same subject.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWING

The invention will now be described in relation to the drawings in which:

FIG. 4 shows a graph illustration the adjuvant activity of compounds 17, 19, 26a, 26b, 33a, 33b and OVA.

DETAILED DESCRIPTION OF THE INVENTION

(i) Definitions

Figure 1:
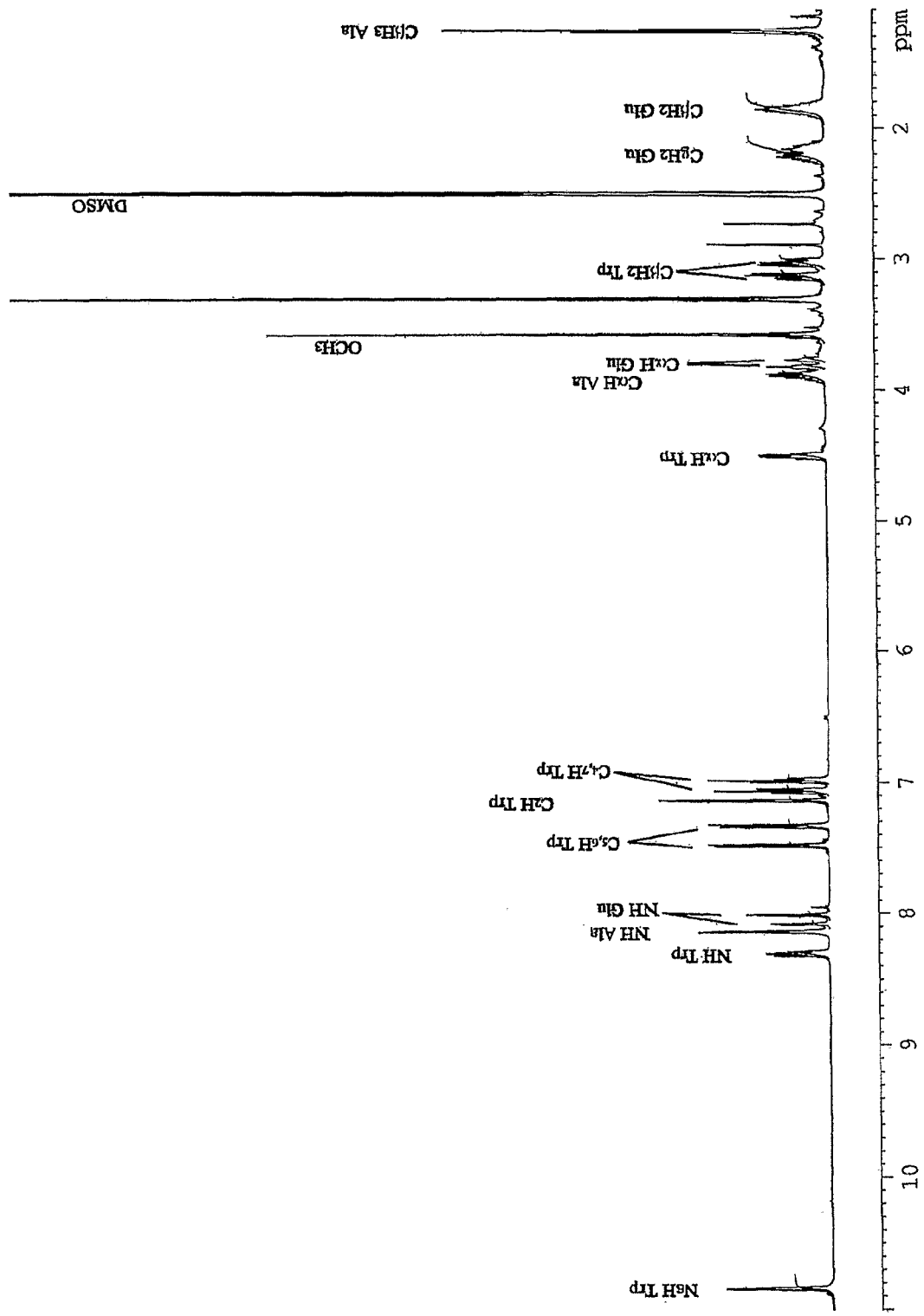
FIG. 1 is a NMR spectrum of cyclo-L-Ala-L-Glu-(L-Trp-OMe), which is a compound of one embodiment of the present invention.

The following standard abbreviations for the amino acid residues are used throughout the specification: Ala—alanine; Arg—arginine; Asn—Asparagine; Asp—aspartic acid; Cys—cysteine; Glu—glutamic acid; iGlu—iso-glutamic acid; Gln—glutamine; His—histidine; Lys—lysine; Met—methionine; Ser—serine; Thr—threonine; Phe—phenylalanine; Gly—glycine; Ile—isoleucine; Leu—leucine; Pro—proline; Val—valine; Nval—N-valine; Trp—tryptophan; and Tyr—tyrosine.

The term "Ph" means phenyl.

The term "Bn" means benzyl.

The term "Me" means methyl.

The term "alkyl" as used herein means straight and/or branched chain alkyl groups containing from one to six carbon atoms and includes methyl, ethyl, propyl, isopropyl, t-butyl, pentyl, hexyl and the like.

The term "alkoxy" as used herein means straight and/or branched chain alkoxy groups containing from one to six carbon atoms and includes methoxy, ethoxy, propyloxy, isopropyloxy, t-butoxy, hexyloxy and the like.

The term "alkenyl" as used herein means straight and/or branched chain alkenyl groups containing from two to six carbon atoms and one to three double bonds and includes vinyl, allyl, 1-butenyl, 2-hexenyl and the like.

The term "alkenyloxy" as used herein means straight and/ or branched chain alkenyloxy groups containing from two to six carbon atoms and one to three double bonds and includes vinyloxy, allyloxy, propenyloxyl, butenyloxy, hexenyloxy and the like.

The term "alkylene" as used herein means bifunctional straight and/or branched alkyl radicals containing the specified number of carbon atoms.

The term "halo" as used herein means halogen and includes chloro, fluoro, bromo, iodo and the like.

The term "pharmaceutically acceptable" means compatible with the treatment of animals, in particular, humans.

The term "pharmaceutically acceptable salt" means an acid addition salt or basic addition salt which is suitable for or compatible with the treatment of animals, in particular, humans.

The term "pharmaceutically acceptable acid addition salt" as used herein means any non-toxic organic or inorganic salt of any base compound of the invention, or any of its intermediates. Basic compounds of the invention that may form an acid addition salt include those having a basic nitrogen, for example $NH_2$ and $NHC_{1-4}$alkyl. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of the compounds of the invention are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of the compounds of the invention, for laboratory use, or for subsequent conversion to a pharmaceutically acceptable acid addition salt.

The term "pharmaceutically acceptable basic addition salt" as used herein means any non-toxic organic or inorganic base addition salt of any acid compounds of the invention. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art.

The term "solvate" as used herein means a compound of the invention, or a pharmaceutically acceptable salt of a compound of the invention, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

The term "compound(s) of the invention" as used herein means compound(s) of Formula I, and/or pharmaceutically acceptable salts, solvates and/or prodrugs thereof.

It is to be clear that the present invention includes pharmaceutically acceptable salts, solvates and prodrugs of compounds of the invention and mixtures comprising two or more compounds of the invention, pharmaceutically acceptable salts of the compounds of the invention (where applicable), pharmaceutically acceptable solvates of the compounds of the invention and prodrugs of the compounds of the invention.

The term an "effective amount" or a "sufficient amount" of an agent as used herein is that amount sufficient to effect beneficial or desired results, including clinical results, and, as such, an "effective amount" depends upon the context in which it is being applied. For example, in the context of administering an agent that acts as an immunomodulator, an effective amount of an agent is, for example, an amount sufficient to achieve such a modulation in immune response as compared to the response obtained without administration of the agent.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

The term "modulate" as used herein includes the inhibition or suppression of a function or activity (such as immune response) as well as the enhancement of a function or activity.

To "inhibit" or "suppress" or "reduce" a function or activity, such as immune response, is to reduce the function or activity when compared to otherwise same conditions except for a condition or parameter of interest, or alternatively, as compared to another conditions.

To "enhance" or "increase" or "stimulate" a function or activity, such as immune response, is to increase the function or activity when compared to otherwise same conditions except for a condition or parameter of interest, or alternatively, as compared to another conditions.

The term "subject" as used herein includes all members of the animal kingdom including human. The subject is preferably a human.

(ii) Compounds of the Invention

The present invention relates to compounds comprising an immunoregulatory portion, a stabilizer portion and, optionally a further functionally active portion. The portions are together via various linker groups to provide a multifunctional compound that can be used to treat multiple disorders in the same subject.

Accordingly, the present invention includes a multifunctional bioctive compound selected from one or more of a compound of Formula I:

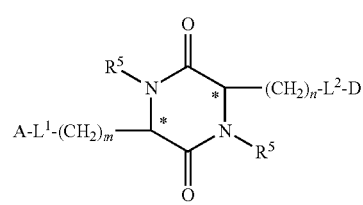

I wherein
A is an immunoregulatory radical selected from the group consisting of Trp, Tyr, Phe, His, aryl and heteroaryl, where the aryl and heteroaryl groups may be optionally substituted with 1 to 6 substituents independently selected from the group consisting of halo, OH, $OC_{1-6}$alkoxy, $C_{1-6}$alkyl, $C_{2-6}$alkenyl, $C_{2-6}$alkenyloxy, $NH_2$, $NH(C_{1-6}$alkyl), $N(C_{1-6}$alkyl)($C_{1-6}$alkyl), CN, $CF_3$, $OCF_3$, $NO_2$, $C(O)C_{1-6}$alkyl, $C(O)OC_{1-6}$alkyl, $SO_2C_{1-6}$alkyl, $SO_2C_{1-6}$alkyl, $SO_2NH_2$, $SO_2NHC_{1-6}$alkyl, phenyl and $C_{1-6}$alkylenephenyl, and where heteroaryl is an aromatic carbocyclic ring containing from 5 to 10 carbon atoms, in which 1 to 4 carbon atoms have been replaced with a heteroatom selected from one or more of O, S and N—$R^1$, where $R^1$ is selected from the group consisting of H, $C_{1-6}$alkyl, $C_{1-4}$alkylenearyl, $C(O)C_{1-6}$alkyl, $C(O)$aryl, $SO_2C_{1-6}$alkyl and $SO_2$aryl when the N atom is $sp^3$ hybridized, or is a lone pair of electrons when the N atom is Sp hybridized;

$L^1$ and $L^2$ are each independently a linker group selected from the group consisting of a single bond, —C(O)— —C(O)$NR^2$—, —$NR^2C(O)$—, —$NR^2$—, —C(O)—O—, —OC(O)—, —S—S—, $SO_2NR^2$—, $NR^2SO_2$, —S— and —O—;

$R^2$ is selected from the group consisting of H, $C_{1-6}$alkyl, $C_{1-6}$alkylenearyl, $C(O)C_{1-6}$alkyl, $C(O)$aryl, $SO_2C_{1-6}$alkyl and $SO_2$aryl;

$R^5$ is H or $C_{1-6}$alkyl;

* is the L or D configuration or mixtures thereof;

m is an integer between 1 and 50;

n is an integer between 0 and 50; and

D is selected from the group consisting of H, $C_{1-6}$alkyl, any side chain of an amino acid and any functionally active molecule, and pharmaceutically acceptable salts, solvates and prodrugs thereof.

In the compounds of the present invention, A is an immunoregulatory radical. The term "immunoregulatory radical" refers to any aromatic- or heteroaromatic-containing group having immuno- or hemosuppressive activity or immuno- or hemostimulative activity. Specifically, A is selected from the group consisting of Trp, Tyr, Phe, His, aryl and heteroaryl, where the aryl and heteroaryl groups may be optionally substituted with 1 to 6 substituents independently selected from the group consisting of halo, OH, $OC_{1-6}$alkoxy, $C_{1-6}$alkyl, $C_{2-6}$alkenyl, $C_{2-6}$alkenyloxy, $NH_2$, $NH(C_{1-6}$alkyl), $N(C_{1-6}$alkyl)($C_{1-6}$alkyl), CN, $CF_3$, $OCF_3$, $NO_2$, $C(O)C_{1-6}$alkyl, $C(O)OC_{1-6}$alkyl, $SO_2C_{1-6}$alkyl, $SO_2NH_2$, $SO_2NHC_{1-6}$alkyl, phenyl and $C_{1-6}$alkylenephenyl, and where heteroaryl is an aromatic carbocyclic ring containing from 5 to 10 carbon atoms, in which 1 to 4 carbon atoms have been replaced with a heteroatom selected from one or more of O, S and N—$R^1$, where $R^1$ is selected from the group consisting of H, $C_{1-6}$alkyl, $C_{1-6}$alkylenearyl, $C(O)C_{1-6}$alkyl, $C(O)$aryl, $SO_2C_{1-6}$alkyl and $SO_2$aryl when the N atom is $sp^3$ hybridized, or is a lone pair of electrons when the N atom is $sp^2$ hybridized. In embodiments of the invention, A is selected from the group consisting of Trp, Tyr, Phe, His, aryl and heteroaryl, where the aryl and heteroaryl groups may be optionally substituted with 1 to 3 substituents independently selected from the group consisting of halo, OH, $OC_{1-4}$alkoxy, $C_{1-4}$alkyl, $C_{2-4}$alkenyl, $C_{2-4}$alkenyloxy, $NH_2$, $NH(C_{1-4}$alkyl), $N(C_{1-4}$alkyl)($C_{1-4}$alkyl), CN, $CF_3$, $OCF_3$, $NO_2$, $C(O)C_{1-4}$alkyl, $C(O)OC_{1-4}$alkyl, $SO_2C_{1-4}$alkyl, $SO_2NH_2$, $SO_2NHC_{1-4}$alkyl, phenyl and $C_{1-4}$alkylenephenyl, and where heteroaryl is an aromatic carbocyclic ring containing from 5 to 10 carbon atoms, in which 1 to 3 carbon atoms have been replaced with a heteroatom selected from one or more of O, S and N—$R^1$, where $R^1$ is selected from the group consisting of H, $C_{1-4}$alkyl, $C_{1-2}$alkylenearyl, $C(O)C_{1-4}$alkyl, $C(O)$aryl, $SO_2C_{1-4}$alkyl and $SO_2$aryl when the N atom is $sp^3$ hybridized, or is a lone pair of electrons when the N atom is $sp^2$ hybridized. In further embodiments of the invention, A is selected from the group consisting of Trp, aryl and heteroaryl, wherein aryl is phenyl or naphthyl and heteroaryl is pyridinyl, imidazolyl, thienyl, furanyl, indolyl, isoquinolinyl, quinolinyl, benzothienyl, benzofuranyl, benzothiazolyl, thiazolo, benzooxazolyl, benzoisoxazolyl, benzoisothiazolyl or the like, with the indole ring of Trp, aryl and heteroaryl being unsubstituted or substituted with 1 to 2 substituents independently selected from the group consisting of halo, OH, $OC_{1-4}$alkoxy, $C_{1-4}$alkyl, $C_{2-4}$alkenyl, $C_{2-4}$alkenyloxy, $NH_2$, $NH(C_{1-4}$alkyl), $N(C_{1-4}$alkyl)($C_{1-4}$alkyl), CN, $CF_3$, $OCF_3$, $NO_2$, $C(O)C_{1-4}$alkyl, $C(O)OC_{1-4}$alkyl, $SO_2C_{1-4}$alkyl, $SO_2NH_2$, $SO_2NHC_{1-4}$alkyl, phenyl and $C_{1-4}$alkylenephenyl.

When A is selected from Trp, Tyr, Phe or His, this group may be connected to the linker via the amine or the carboxyl group. When not connected to the linker, the free amine or carboxyl group may be derivativized. For example, the amine may be mono or dialkylated with $C_{1-6}$alkyl, acylated with a $C(O)C_{1-6}$alkyl or converted to $NH_3^+$ by addition of a pharmaceutically acceptable acid. Further, the carboxyl group may be esterified, for example as a $C_{1-6}$alkyl ester, converted to the corresponding amide which may also be mono- or diesterified with $C_{1-6}$alkyl, converted to its corresponding hydrazine or to its corresponding basic addition salt. In another aspect of the present invention, it has been found that when A is Trp, the immuno- and hemomodulating activity of this group may be controlled by the stereochemistry at the α-carbon. For example, when the stereochemistry is in the D-configuration, this group may possess immuno- and hemodepressant activity and when it is in the L-configuration it may possess immuno- and hemostimulant activity. Accordingly, the immunomodulatory activity of the molecules of the present invention can be controlled and tailored for specific uses and combination therapies.

In an embodiment of the invention, A is a group having the formula II:

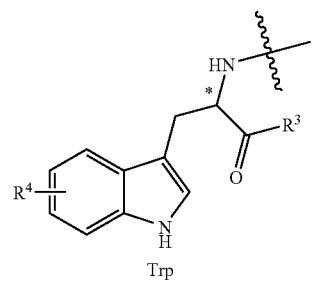

Trp wherein $R^3$ is selected from the group consisting of H, $OC_{1-6}$alkyl, $NH_2$, $NHC_{1-6}$alkyl, $N(C_{1-6}$alkyl$)_2$, $NHNH_2$ and OY, where Y is a pharmaceutically acceptable cation; $R^4$ is 1 to 4 substituents which are independently selected from the group consisting of H, halo, OH, $OC_{1-6}$alkoxy, $C_{1-6}$alkyl, $C_{1-6}$alkenyl, $C_{1-6}$alkenyloxy, $NH_2$, $NH(C_{1-6}$alkyl), $N(C_{1-6}$alkyl)($C_{1-6}$alkyl), CN, $CF_3$, $OCF_3$, $NO_2$, $C(O)C_{1-6}$alkyl, $C(O)OC_{1-6}$alkyl, $SO_2C_{1-6}$alkyl, $SO_2NH_2$, $SO_2NHC_{1-6}$alkyl, phenyl and $C_{1-6}$alkylenephenyl; and

* is the L or D configuration or mixtures thereof.

The present invention includes compounds of Formula I wherein $R^3$ is selected from the group consisting of H, $OC_{1-6}$alkyl, $NH_2$, $NHC_{1-6}$alkyl, $N(C_{1-6}$alkyl$)_2$, $NHNH_2$ and OY, where Y is a pharmaceutically acceptable cation. In embodiments of the invention, $R^3$ is selected from the group consisting of H, $OC_{1-4}$alkyl, $NH_2$, $NHC_{1-4}$alkyl, $N(C_{1-4}$alkyl$)_2$, $NHNH_2$ and OY. In further embodiments of the invention, $R^3$ is selected from the group consisting of H, Me, $NH_2$, NHMe, $NMe_2$, $NHNH_2$ and OY. The cation "Y" may be any pharmaceutically acceptable cation, for example $Na^+$, $K^+$ and $Zn^{2+}$.

The compounds of Formula I also include those in which $R^4$ is 1 to 4 substituents which are independently selected from the group consisting of H, halo, OH, $OC_{1-6}$alkoxy, $C_{1-6}$alkyl, $C_{1-6}$alkenyl, $C_{1-6}$alkenyloxy, $NH_2$, $NH(C_{1-6}$alkyl), $N(C_{1-6}$alkyl)($C_{1-6}$alkyl), CN, $CF_3$, $OCF_3$, $NO_2$, $C(O)C_{1-6}$alkyl, $C(O)OC_{1-6}$alkyl, $SO_2C_{1-6}$alkyl, $SO_2NH_2$, $SO_2NHC_{1-6}$alkyl, phenyl and $C_{1-6}$alkylenephenyl. In embodiments of the invention, $R^4$ is 1 to 3 substituents which are independently selected from the group consisting of H, halo, OH, $OC_{1-4}$alkoxy, $C_{1-4}$alkyl, $C_{2-4}$alkenyl, $C_{2-4}$alkenyloxy, $NH_2$, NH($C_{1-4}$alkyl), N($C_{1-4}$alkyl)($C_{1-4}$alkyl), CN, $CF_3$, $OCF_3$, $NO_2$, $C(O)C_{1-4}$alkyl, $C(O)OC_{1-4}$alkyl, $SO_2C_{1-4}$alkyl, $SO_2NH_2$, $SO_2NHC_{1-4}$alkyl, phenyl and $C_{1-4}$alkylenephenyl. In further embodiments of the invention, $R^4$ is 1 to 3 substituents which are independently selected from the group consisting of H, halo, OH, OMe, Me, vinyl, vinyloxy, $NH_2$, NHMe, $NHMe_2$, CN, $CF_3$, $OCF_3$, $NO_2$, C(O)Me, C(O)OMe, $SO_2Me$, $SO_2NH_2$, $SO_2NHMe$, phenyl and benzyl. In still further embodiments of the invention, $R^4$ is a substituent selected from the group consisting of H, halo, OH, OMe, Me, vinyl, vinyloxy, $NH_2$, NHMe, $NHMe_2$, CN, $CF_3$, $OCF_3$, $NO_2$, C(O)Me, C(O)OMe, $SO_2Me$, $SO_2NH_2$, $SO_2NHMe$, phenyl and benzyl. In even further embodiments of the invention, $R^4$ is H.

In the multifunctional bioactive compounds of the present invention, each of $L^1$ and $L^2$ is a linker group independently selected from the group consisting of a single bond, —C(O)—, —C(O)$NR^2$—, —$NR^2$C(O)—, —$NR^2$—, —C(O)—O—, —OC(O)—, —S—S—, $SO_2NR^2$—, $NR^2SO_2$, —S— and —O—, where $R^2$ is selected from the group consisting of H, $C_{1-6}$alkyl, $C_{1-6}$alkylenearyl, $C(O)C_{1-6}$alkyl, C(O)aryl, $SO_2C_{1-6}$alkyl and $SO_2$aryl. In embodiments of the invention, each of $L^1$ and $L^2$ is independently selected from the group consisting of a single bond, —C(O)—, —C(O)$NR^2$—, —$NR^2$C(O)—, —$NR^2$—, —C(O)—O—, —OC(O)— and —O—. In further embodiments of the invention, each of $L^1$ and $L^2$ is independently selected from the group consisting of —C(O)—, —$NR^2$—, —C(O)$NR^2$— and —$NR^2$C(O)—. In other embodiments of the invention, $R^2$ is selected from the group consisting of H, $C_{1-4}$alkyl, $C_{1-4}$alkylenearyl, $C(O)C_{1-4}$alkyl, C(O)Ph, $SO_2C_{1-4}$alkyl and $SO_2$Ph. In still further embodiments of the invention, $R^2$ is selected from the group consisting of H, Me, Bn, C(O)Me, C(O)Ph, $SO_2Me$ and $SO_2$Ph. In even further embodiments of the invention, $R^2$ is H.

In the bioactive compounds of the invention, m is an integer between 1 and 50. In embodiments of the invention, m is an integer between 1 and 25. In further embodiments of the invention, m is an integer between 1 and 10. In still further embodiments of the invention, m is an integer between 1 and 6.

The multifunctional bioactive compounds of the invention include those where n is an integer between 0 and 50. In embodiments of the invention, n is an integer between 0 and 25. In further embodiments of the invention, n is an integer between 0 and 10.

The compounds of Formula I, include those in which $R^5$ is selected from the group consisting of H and $C_{1-6}$alkyl and * represents the D or L configuration or mixtures thereof. In embodiments of the invention, $R^5$ is selected from H and $C_{1-4}$alkyl, specifically H and Me. In further embodiments of the invention, both are substantially in the D configuration or both are substantially in the L configuration.

The multifunctional bioactive compounds of the invention also include those where D is selected from the group consisting of H, $C_{1-6}$alkyl, any side chain of an amino acid and any functionally bioactive molecule. In embodiments of the invention, D is selected from the group consisting of H, $C_{1-4}$alkyl, any side chain of an amino acid and any functionally active molecule. By functionally bioactive molecule, it is meant any molecule having a pharmacological effect in the subject. This pharmacological effect may be one which complements, enhances or synergizes with the immunoregulatory group A, or it may provide another therapeutic action so that when the bioactive compounds of the invention are administered to the subject, combination therapy is effected. More than one functionally bioactive molecule may be used. Examples of functionally active molecules include, but are not limited to, adjuvants such as palmitoyl; analgesics such as peptide analgesics; opiates and antidotes such as dermorphin, morphine, naloxone and derivatives thereof; synthetic vaccines such as antigenic determinants—T- and B-epitopes; antibiotics, such as fusidic acid, pharmaceutical pharmacophores including small molecules such as methotrexate, diclophenac, ibuprophen, indometacine, naproxen, ketoprofen; sugars; lipids; and nucleotides.

In an embodiment of the present invention, the multifunctional bioactive compounds of Formula I have the following formula:

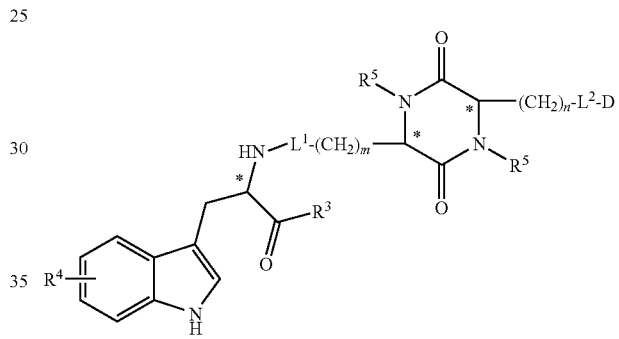

wherein $L^1$, $L^2$, D, $R^3$, $R^4$, $R^5$, m, n and * have the meanings provided above.

In a further embodiment of the invention, the multifunctional bioactive compounds of Formula I have the following formula:

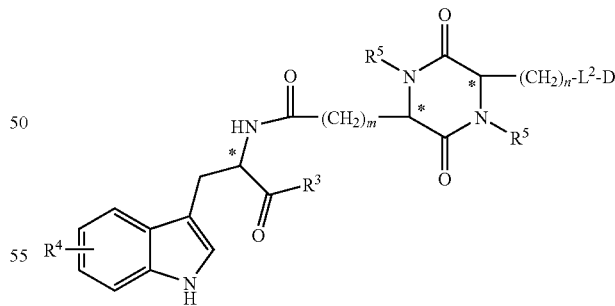

wherein $L^2$, D, $R^3$, $R^4$, $R^5$, m, n and * have the meanings provided above.

Examples of multifunctional bioactive compounds and pharmaceutically acceptable salts, solvates and prodrugs thereof, representing specific embodiments of the present invention are shown in Tables 1 and 9.

All of the compounds of the invention have more than one asymmetric centre. Where the compounds according to the invention possess more than one asymmetric centre, they may exist as diastereomers. It is to be understood that all such isomers and mixtures thereof in any proportion are encompassed within the scope of the present invention. It is to be understood that while the relative stereochemistry of the compounds of the invention may be as shown in any given compound shown herein, such compounds of the invention may also contain certain amounts (e.g. less than 20%, preferably less than 10%, more preferably less than 5%) of compounds of the invention having alternate stereochemistry.

The compounds of the invention can be prepared from known starting materials using procedures known in the art. Generally, the compounds are prepared by the coupling of two or more entities together, for example, using standard coupling chemistry (e.g. formation of peptide bonds, amide linkages, disulfide linkages, ester linkages, etc.). The diketopiperazine moiety may be prepared using known chemistry. For example, diketopiperazines can be formed by cyclodimerization of amino acid ester derivatives as described by Katchalski et al. in J. Amer. Chem. Soc., 68, 879-880 (1946), by cyclization of dipeptide ester derivatives, or by thermal dehydration of amino acid derivatives and high boiling solvents as described by Kopple et al. in J. Org. Chem., 33 (2), 862-864 (1968).

In some cases, the chemistries used to prepare the compounds of the invention may have to be modified, for instance, by use of protective groups, to prevent side reactions due to reactive groups, such as reactive groups attached as substituents. This may be achieved by means of conventional protecting groups, for example as described in "Protective Groups in Organic Chemistry" McOmie, J. F. W. Ed., Plenum Press, 1973 and in Greene, T. W. and Wuts, P.G.M., "Protective Groups in Organic Synthesis", John Wiley & Sons, $3^{rd}$ Edition, 1999.

The formation of a desired compound salt is achieved using standard techniques. For example, the neutral compound is treated with an acid or base in a suitable solvent and the formed salt is isolated by filtration, extraction or any other suitable method.

The formation of solvates of the compounds of the invention will vary depending on the compound and the solvate. In general, solvates are formed by dissolving the compound in the appropriate solvent and isolating the solvate by cooling or using an antisolvent. The solvate is typically dried or azeotroped under ambient conditions.

The present invention includes within its scope, prodrugs of the compounds of the invention. In general, such prodrugs will be functional derivatives of a compound of the invention which are readily convertible in vivo into the compound from which it is notionally derived. Prodrugs of the compounds of the invention may be conventional esters formed with available hydroxy, thiol, amino or carboxyl group. For example, an available OH or $NH_2$ group in a compound of the invention may be acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters. In further embodiments, the prodrugs of the compounds of the invention are those in which one or more of the hydroxy groups in the compounds is masked as groups which can be converted to hydroxy groups in vivo. Conventional procedures for the selection and preparation of suitable prodrugs are described, for example, in "Design of Prodrugs" ed. H. Bundgaard, Elsevier, 1985.

The present invention includes radiolabeled forms of compounds of the invention, for example, compounds of the invention labeled by incorporation within the structure $^3$H or $^{14}$C or a radioactive halogen such as $^{125}$I. A radiolabeled compound of the invention may be prepared using standard methods known in the art. For example, tritium may be incorporated into a compound of the invention using standard techniques, for example, by hydrogenation of a suitable precursor to a compound of the invention using tritium gas and a catalyst. Alternatively, a compound of the invention containing radioactive iodo may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethylditin in the presence of tetrakis(triphenylphosphine) palladium (0) in an inert solvent, such as dioxane, and at elevated temperatures, suitably about 50 to 100° C.

(iii) Uses

The present invention provides novel compounds of the Formula I. Accordingly, the present invention includes all uses of the compounds of the invention including their use in therapeutic methods and pharmaceutical compositions, their use in diagnostic assays and their use as research tools.

The present invention in particular relates to pharmaceutical compositions comprising a multifunctional bioactive compound of the invention and a pharmaceutically acceptable carrier.

Also included in the present invention are methods of treating immune disorders, and optionally other disorders in the same subject, comprising administering an effective amount of a multifunctional bioactive compound of the invention to a subject in need thereof. Further, there is provided a use of a multifunctional bioactive compound of the invention to treat immune disorders, and optionally other disorders in the same subject, as well as a use of a multifunctional bioactive compound of the invention to prepare a medicament to treat immune disorders, and optionally other disorders in the same subject.

In one aspect, the invention provides a method of modulating the immune system and/or hemopoiesis in an animal comprising administering an effective amount of a multifunctional bioactive compound of the invention to a subject in need thereof.

In an embodiment of the invention, there is provided a method of stimulating the immune system comprising administering an effective amount of a multifunctional bioactive compound of the invention to a subject in need thereof. In another embodiment, the invention provides a method of restoring hemopoiesis in an animal with impaired hemopoiesis, for example caused by irradiation or cytostatic agents, comprising administering an effective amount of a multifunctional bioactive compound of the invention to a subject in need thereof.

In yet another embodiment, the invention provides a method of treating hemopoietic disorders, for example, without limiting to, immune cytopenia, multiple myeloma, chronic lymphoid leucosis, lymphocytic lymphomas, lymphosarcomas and in particular, B-cellular lymphoid leucosis, comprising administering an effective amount of a multifunctional bioctive compound of the invention to a subject in need thereof.

In another embodiment, the invention provides a method for treating immune and/or hemopoietic disorders such as cancer in an animal comprising administering an effective amount of a multifunctional bioactive compound of the invention to a subject in need thereof, possibly in combination with a cytostatic agent. The cytostatic agent may be, for example, oxyurea or hyperthermia.

In yet another embodiment, the invention also relates to a method of immunosuppressing an immune system in an animal comprising administering an effective amount of a multifunctional bioactive compound of the invention to a subject in need thereof. In one embodiment, the compound may be administered prior to an organ or bone marrow transplant. The immunoregulatory properties of the compounds of the invention may be controlled, for example, by the stereochemistry in the "A" portion and "*" of the compound.

The compounds of the invention may be used in the form of the free base, free acid, in the form of salts, solvates and/or prodrugs. All forms are within the scope of the invention.

In accordance with the methods of the invention, the described compounds, salts, prodrugs or solvates thereof may be administered to a patient in a variety of forms depending on the selected route of administration, as will be understood by those skilled in the art. The compositions of the invention may be administered, for example, by oral, parenteral, buccal, sublingual, nasal, rectal, patch, pump or transdermal (topical) administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be administered by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like.

A compound of the invention may also be administered parenterally. Solutions of a compound of the invention can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases, the forms must be sterile and must be fluid to the extent that easy syringability exists. Ampoules are convenient unit dosages.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Compositions for topical administration may include, for example, propylene glycol, isopropyl alcohol, mineral oil and glycerin. Preparations suitable for topical administration include liquid or semi-liquid preparations such as liniments, lotions, applicants, oil-in-water or water-in-oil emulsions such as creams, ointments or pastes; or solutions or suspensions such as drops. In addition to the aforementioned ingredients, the topical preparations may include one or more additional ingredients such as diluents, buffers, flavoring agents, binders, surface active agents, thickeners, lubricants, preservatives, e.g. methyl hydroxybenzoate (including antioxidants), emulsifying agents and the like.

Sustained or direct release compositions can be formulated, e.g. liposomes or those wherein the active compound is protected with differentially degradable coatings, such as by microencapsulation, multiple coatings, etc. It is also possible to freeze-dry the compounds of the invention and use the lypolizates obtained, for example, for the preparation of products for injection.

The compounds of the invention may be administered to an subject alone or in combination with pharmaceutically acceptable carriers, as noted above, the proportion of which is determined by the solubility and chemical nature of the compound, chosen route of administration and standard pharmaceutical practice.

The dosage of the compounds and/or compositions of the invention can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skilled in the art can determine the appropriate dosage based on the above factors. For example, in the topical treatment, ointments, creams or lotions containing from 1-1000 µg/g of a compound of the invention may be administered. Oral preparations may be formulated, preferably as tablets, capsules, or drops, containing from 0.5-1000 µg of a compound of the invention per dosage unit. The compounds of the invention may be administered initially in a suitable dosage that may be adjusted as required, depending on the clinical response. For ex vivo treatment of cells over a short period, for example for 30 minutes to 1 hour or longer, higher doses of compound may be used than for long term in vivo therapy.

In addition to the above-mentioned therapeutic uses, the compounds of the invention are also useful in diagnostic assays, screening assays and as research tools.

In diagnostic assays, the compounds of the invention may be useful in identifying or detecting an immune disorder. In such an embodiment, the compounds of the invention may be radiolabeled (as hereinbefore described) and contacted with a population of cells. The presence of the radiolabel on the cells may indicate an immune disorder.

In screening assays, the compounds of the invention may be used to identify other compounds that modulate immune responses. In such assays, the compounds may also be radio-labeled.

The following non-limiting examples are illustrative of the present invention:

EXAMPLES

Materials and Methods

NMR experiments were performed on Bruker Avance DRX 500 spectrometer. The spectra were acquired in 0.6 µl $(CD_3)_2SO$ at 30° C. (99.95% Deuterium, Deiton, S. Peterburg). A relaxation delay of 5.0 s was used. The $^1H$ chemical shifts were determined relative to those (arbitrary chosen as 2.5 ppm at 30° C.) of the $(CH_3)_2SO$ signal.

HPLC analyses were performed on System Gold Beckman analytical gradient chromatographic device. Column Ultrasphere-ODS, 5µ, 205×4.6 mm. Detection—UV spectrophotometer, λ 214 nm. Ambient temperature. Gradient 0.02M triethylammonium phosphate buffer (pH=3.0) in acetonitrile (from 0% buffer A to 100% buffer B). Buffer A—15% of 0.02M triethylammonium phosphate in acetonitrile. Buffer B—50% of 0.02M triethylammonium phosphate in acetonitrile.

Mass spectra were acquired on a VISION 2000 MALDI mass spectrometer.

Example 1

Preparation of Cyclo-L-Ala-L-Glu(OH)

(a) Preparation of Boc-L-Ala-L-Glu(OBzl)-OH

Boc-L-Ala-ONSu (56.5 g, 0.1 mol) and 26.1 g (0.11 mol) of H-L-Glu(OBzl)-OH were mixed with 500 ml of dioxin/water (1:1) and N-methylmorpholine (11.7 ml) until the mixture reached a pH of about 9 to 9.2. The suspension was dissolved after 12 to 18 hours at room temperature. Solvents were evaporated in vacuum and the residual oil was dissolved in 500 ml of EtOAc which was then transferred into a separating funnel and washed with 3×200 ml of 5% $H_2SO_4$ in water to neutral pH. The organic layer was separated and dried with anhydrous sodium sulfate. After drying, EtOAc was evaporated in vacuum. The crude product was an oil and the yield was 40.5 g (~100%). $R_f$=0.6 ($CHCl_3$:Et-Ac:MeOH=6:3:1).

(b) Preparation of Boc-L-Ala-L-Glu(OBzl)-ONp

Boc-L-Ala-L-Glu(OBzl)-OH (40.5 g, 0.1 mol) was dissolved in 300 ml of EtOAc and combined with 17 g (0.12 mol) of p-nitrophenol. The reaction was kept at 0° C. for 1 hour. DCC (24.7 g, 0.12 mol) was then added. The reaction was stirred for 1 hour at 0° C. and for 4 hours at room temperature. The precipitate of DCU was filtered off and the solvent was evaporated in vacuum. The residual oil was then dissolved in ether. The precipitate was filtered off and washed with ether and hexane. The yield was 35 g (64%). $R_f$=0.7 ($CHCl_3$:Et-Ac:MeOH=6:3:1).

(c) Preparation of cyclo-L-Ala-L-Glu(OBzl)

Boc-L-Ala-L-Glu(OBzl)-ONp (56.0 g, 0.1 mol) was dissolved and cooled to −15° C. TFA was added and the mixture was stirred for 1 hour and gradually warmed to room temperature. Completion of the reaction was monitored by TLC using the system $CHCl_3$:Et-OAc:MeOH=6:3:1. After completion of the reaction, the mixture was evaporated in vacuum, then twice evaporated with iso-propanol and dissolved in 500 ml of EtOAc. N-methylmorpholine was added until the mixture reached a pH level of 9 to 9.5. After 12 hours, the cyclo-L-Ala-L-Glu(OBzl) precipitated. The precipitate was filtered off, washed with EtOAc, ether and hexane. The yield was 21.0 g (70%). $R_f$=0.55 ($CHCl_3$:EtOAc:MeOH:AcOH=6:3:1:0.1); HPLC data: retention time 15.9 min.

(d) Preparation of cyclo-L-Ala-L-Glu(OH)

Cyclo-L-Ala-L-Glu(OBzl) (14.5 g, 0.05 mol) was dissolved in 200 ml of trifluorethanol and then 1.5 g of palladium black was added. Hydrogen was bubbled through the suspension and the mixture was stirred for 48 hours. The completion of the reaction was monitored by TLC. After the reaction was complete, the catalyst was filtered off and the solvent was evaporated in vacuum. The residual peptide was dissolved in 200 ml of distilled water and the impurities were extracted with 3×100 ml of EtOAc. The water phase was combined and evaporated in vacuum. The precipitate was washed with ether and hexane and then dried in air. The yield was 10.2 g (94%). $R_f$=0.2($CHCl_3$ EtOAc:MeOH:AcOH=6:3:1:0.1); $R_f$=0.5 ($CHCl_3$:EtOAc:MeOH: 32% Ac OH=6:3:1:0.1); HPLC data: retention time 6.7 min.

Example 2

Preparation of Cyclo-L-Ala-L-Glu-(L-Trp-Oh)

(a) Preparation of cyclo-L-Ala-L-Glu-(L-Trp-OMe)

Cyclo-L-Ala-L-Glu-(OH) (2.2 g, 0.01 mol) was dissolved in 50 ml DMF and then heated to 60° C. After the peptide was dissolved, the mixture was cooled to −15° C. Cooled to −15° C. iso-butylchlorophormate (1.5 ml, 0.012 mol) was added, followed by the addition of 1.4 ml (0.012 mol) of N-methylmorpholine. The reaction was stirred for 5 min at −15° C. and a solution of 2.8 g (0.011 mol) of HCl H-L-Trp-OMe in 20 ml of DMF and 1.4 ml (0.012 mol) of N-methylmorpholine, both cooled to −15° C., were added. After 1 hour of stirring at 0° C., the reaction was heated gradually to room temperature over 4 hours. The precipitate was filtered off and the solvent was evaporated in vacuum. The residual oil was dissolved in 100 ml mixture of n-butanol/water and transferred to a separation funnel. The organic layer was separated and washed with 3×50 ml of 5% $H_2SO_4$ and 3×50 ml of 5% $NaHCO_3$ in water. N-butanol was evaporated in vacuum and ether was added to the residual oil. The precipitate was filtered off and washed with ether and hexane. The yield was 3.4 g (80%). $R_f$=0.7 ($CHCl_3$:Et-Ac:MeOH:AcOH=6:3:1:0.1); HPLC data: retention time 16.6 min. The spectrum of cyclo-L-Ala-L-Glu-(L-Trp-OMe) is presented in FIG. 1.

(b) Preparation of cyclo-L-Ala-L-Glu-(L-Trp-OH)

Cyclo-L-Ala-L-Glu-(L-Trp-OMe) (1.1 g, 0.0025 mol) was suspended in 50 ml of EtOH and 0.15 g of NaOH (0.0075 mol) in 25 ml of water was added. The mixture was stirred for ~2 hours. After completion of the reaction, HCl was added until the mixture reached a pH of about 7. The solvent was evaporated in vacuum. The residual mixture was transferred to a separation funnel and 50 ml of n-butanol and water with pH=3 was added. The organic layer was separated, washed with water to neutral pH and then evaporated in vacuum. The residue was evaporated twice with iso-propanol and then ether was added. The precipitate was filtered off and washed with ether and hexane. The yield was 0.9 g (82%). $R_f=0.5$ (CHCl$_3$:Et-Ac:MeOH:AcOH=6:3:1:0.1); HPLC data: retention time 9.3 min.; mass spectrum data: [M+H$^+$+Na]=407.7.

In a like manner, the following additional compounds were prepared. Mass spectrum data for some of these compounds are provided below.

Cyclo-L-Ala-L-Glu-(L-Trp-OMe)
Cyclo-L-Ala-L-Glu-(L-Trp-OH): Mass spectrum data: [M+H$^+$+Na]=407.7
Cyclo-D-Ala-D-Glu-(D-Trp-OMe)
Cyclo-D-Ala-D-Glu-(D-Trp-OH): Mass spectrum data: [M+H$^+$+Na]=407.9
Cyclo-L-Ala-L-Glu-(D-Trp-OMe)
Cyclo-L-Ala-L-Glu-(D-Trp-OH): Mass spectrum data: [M+H$^+$+Na]=408.1
Cyclo-D-Ala-D-Glu-(L-Trp-OMe)
Cyclo-D-Ala-D-Glu-(L-Trp-OH): Mass spectrum data: [M+H$^+$+Na]=407.6
Cyclo-D-Ala-D-Asp-(D-Trp-OMe)
Cyclo-D-Ala-D-Asp-(D-Trp-OH): Mass spectrum data: [M+H$^+$+Na]=394.1
Cyclo-D-Ala-D-Asp-(L-Trp-OMe)
Cyclo-D-Ala-D-Asp-(L-Trp-OH): Mass spectrum data: [M+H$^+$+Na]=394.7
Cyclo-L-Ala-L-Asp-(D-Trp-OMe)
Cyclo-L-Ala-L-Asp-(D-Trp-OH)
Cyclo-L-Ala-L-Asp-(L-Trp-OMe)
Cyclo-L-Ala-L-Asp-(L-Trp-OH): Mass spectrum data: [M+H$^+$+Na]=395.3

Example 3

Preparation of cyclo-L-Lys(H$_2$N)-L-Glu-(L-Trp-NH$_2$)

(a) Preparation of Fmoc-L-Lys(Boc)-L-Glu(OBzl)-OH

Fmoc-L-Lys(Boc)-ONSu (56.5 g, 0.1 mol) and 26.1 g (0.11 mol) of H-L-Glu(OBzl)-OH were mixed with 500 ml of dioxin/water (1:1) and N-methylmorpholine (11.7 ml) until the mixture reached a pH of about 9 to 9.2. After 12 to 18 hours at room temperature, the suspension was dissolved. The solvents were evaporated in vacuum. The residual oil was then dissolved in 500 ml of EtOAc, which was then transferred into a separating funnel and washed with 3×200 ml of 5% H$_2$SO$_4$ in water to neutral pH. The organic layer was separated and dried with anhydrous sodium sulfate. After drying, the EtOAc was evaporated in vacuum. The crude product was an oil and the yield was 69.0 g (~100%). $R_f=0.8$ (CHCl$_3$:Et-Ac:MeOH=6:3:1).

(b) Preparation of H-L-Lys(Boc)-L-Glu(OBzl)-OH

Fmoc-L-Lys(Boc)-L-Glu(OBzl)-OH (69.0 g, 0.1 mol) was dissolved in 300 ml of 20% piperidine in dioxane and stirred for 1 hour at room temperature. The solvent was evaporated in vacuum and residual oil was dissolved in 0.1% AcOH. The precipitate was filtered off and washed with 0.1% AcOH and water to neutral pH. The yield was 43.7 (94%). $R_f=0.5$ (CHCl$_3$:MeOH: 32% AcOH=5:3:1).

(c) Preparation of cyclo-L-Lys(Boc)-L-Glu(OBzl)

H-L-Lys(Boc)-L-Glu(OBzl)-OH (23.0, 0.05 mol) was dissolved in 100 ml of pyridine and refluxed for 4 hours. The reaction was monitored by TLC using the system of CHCl$_3$: MeOH: 32% AcOH=5:3:1. After completion of the reaction, the mixture was evaporated in vacuum and 500 ml of 0.1% AcOH was added. The cyclo-L-Lys(Boc)-L-Glu(OBzl) was precipitated. The precipitate was filtered off, washed with water and dried in a vacuum oven at 40° C. The yield was 20.9 (86%). $R_f=0.75$ (CHCl$_3$:MeOH: 32% AcOH=5:3:1); HPLC data: retention time 19.2 min.

(d) Preparation of cyclo-L-Lys(Boc)-L-Glu(OH)

Cyclo-L-Lys(Boc)-L-Glu(OBzl) (22.2 g, 0.05 mol) was dissolved in 200 ml of trifluorethanol and 1.5 g of palladium black was added. Hydrogen was bubbled through the suspension with stirring for 48 hours. The reaction was monitored by TLC. After the reaction was complete, the catalyst was filtered off and the solvent was evaporated in vacuum. The residual peptide was dissolved in 200 ml of distilled water and the impurities were extracted with 3×100 ml of EtOAc. The water phase was combined and evaporated in vacuum. The precipitate was washed with ether and hexane and dried in air. The yield was 16.7 g (90%). $R_f=0.4$ (CHCl$_3$:EtOAc:MeOH: 32% AcOH=6:3:1:0.1); HPLC data: retention time 12.7 min.

(e) Preparation of cyclo-L-Lys(Boc)-L-Glu-(L-Trp-NH$_2$)

Cyclo-L-Lys(Boc)-L-Glu-(OH) (3.7 g, 0.01 mol) was dissolved in 50 ml pyridine and 0.012 mol of TBTU was added, followed by the addition of 1.4 ml (0.012 mol) of N-methylmorpholine. The reaction was stirred for 5 min at room temperature and a solution of 2.8 g (0.011 mol) of HCl.H-L-Trp-NH$_2$ in 20 ml of pyridine and 1.4 ml (0.012 mol) of N-methylmorpholine were added. The reaction was monitored by TLC. After 4 hours of stirring, the solvent was evaporated in vacuum and the residual oil was dissolved in 100 ml mixture of n-butanol/water and transferred to a separation funnel. The organic layer was separated and washed with 3×50 ml of 5% H$_2$SO$_4$ and 3×50 ml of 5% NaHCO$_3$ in water. N-butanol was evaporated in vacuum and ether was added to the residual oil. The precipitate was filtered off and washed with ether, and hexane. The yield was 5.0 g (88%). $R_f=0.6$ (CHCl$_3$:EtOAc:MeOH:32% AcOH=6:3:1:0.1); HPLC data: retention time 18.6 min.

(f) Preparation of cyclo-L-Lys(H$_2$N)-L-Glu-(L-Trp-NH$_2$)

Cyclo-L-Lys(Boc)-L-Glu-(L-Trp-NH$_2$) (2.9 g, 0.005 mol) was dissolved in 50 ml of 50% TFA/CH$_2$Cl$_2$ containing 0.1% of dithyotreitol. The mixture was stirred for ~1 hour. After completion of the reaction, the solvents were evaporated in vacuum. The residual oil was dissolved in 50 ml of water and transferred to a separation funnel. Ethyl acetate (50 mL) was added. The residual impurities were extracted. The organic layer was separated and then discarded. The water was evaporated and the oil was dissolved in 50 ml of distilled water and lyophilized. The yield was 2.7 g (92% as trifluoroacetate). $R_f=0.35$ (CHCl$_3$:Et-Ac:MeOH:AcOH=6:3:1:0.1); HPLC data: retention time 7.9 min.

Example 4

Effects of Immunosuppressive Agents In Vivo

The effect of tested substances on intact bone marrow was studied in vivo. The peptides were introduced into mice in different manners: injected subcutaneously, intraperitoneally (IP) or introduced per os to intact donor mice, in the doses of 10-1000 µg/kg. Two days after administration of preparation, the mice were killed. Bone marrow suspension was prepared and injected intravenously to lethally irradiated mice. The colony forming activity was evaluated at day 8. Test animals were (CBA×C57B1) F1 mice (30 mice per trial, average from 3 tests).

As can be seen from Table 2, it was found that introduction of thymodepressin and the novel cyclopeptides of the present invention into intact mice decreased the CFU-S population in the bone marrow.

A comparison of the activities of the novel cyclopeptides of the present invention and thymodepressin on suppression of the CFU-S population in the bone marrow is shown in Table 3.

Example 5

Effects of Immunostimulant Agents In Vivo

A study to compare the activity of Neogen and the new cyclic peptides of the present invention in reducing the harmful effects of ionizing radiation was performed.

In this study, the method of exogenous spleen colonies was applied. A suspension of intact bone marrow cells was irradiated ex vivo in the dose of 1 Gy. Different doses of Neogen or cyclic peptides were injected IP, 1M, subcutaneous or introduced per os to lethally irradiated recipients within an hour after the injection of irradiated bone marrow. Colonies were counted on day 8. All data in each group was the mean of three tests.

The data in Table 4 shows that Neogen can stimulate the regeneration process after the detrimental effect of radiation on hemopoietic precursor cells. This process was shown to be effective with 1M or IP injection, but not via per os administration. New cyclic peptides under investigation possessed the same range of activity during systemic administration and are orally active at the dose range of 10-100 µg/kg.

Example 6

Adjuvant Activity of cyclo-L-Ala-L-Glu-(L-Trp-ONa)

Adjuvant activity was tested on 5 groups of mice (C57B16). Each group consisted of 5 animals. Three immunizations were performed:
First Immunization:
  1. Group with Complete Freund's Adjuvant (CFA)
  2. Group with ovalbumin (OVA egg) (25 micrograms/mouse)
  3. Group with CFA+ovalbumin (25 micrograms/mouse)
  4. Group with ovalbumin (25 micrograms/mouse)+peptide 1 microgram/mouse
  5. Group with ovalbumin (25 micrograms/mouse)+peptide 10 micrograms/mouse
Second Immunization:
  The same set 21 days after first immunization by injection of 12.5 micrograms of ovalbumin/mouse to groups 2-5.
Third Immunization:
  The same set 35 days after first immunization by injection of 12.5 micrograms of ovalbumin/mouse to groups 2-5.
  On day 42, the total blood from each mouse was collected. The blood was pooled from each group of mice. The stimulation index of each group was compared. The stimulation index was calculated as a ratio between optical density (OD=1) of diluted pools of groups 3-5 to the optical density (OD=1) of diluted pools of group 2 (control with no adjuvant).

As can be seen in Table 5, the results of this experiment show that cyclopeptide Cyclo-L-Ala-L-Glu-(L-Trp-ONa) alone, even without further modification by coupling sugar or palmitoyl function, possesses adjuvant activity and increases by 74% titers of antibodies to ovalbumin.

Example 7

Adjuvant Activity of cyclo-L-Ala-L-Glu-(L-Trp-OH) (Compound 17)

Adjuvant activity was tested on 6 groups of mice. Each group consisted of 5 animals. Three immunizations were performed as follows:
First Immunization:
  1. Mouse Nos. 1 to 5—Complete Freund's adjuvant (CFA=control)
  2. Mouse Nos. 6 to 10—ovalbumin (OVA egg) 25 micrograms per animal+adjuvant 100 micrograms per animal
  3. Mouse Nos. 11 to 15—ovalbumin 25 micrograms per animal+CFA
  4. Mouse Nos. 16 to 20—ovalbumin 25 micrograms per animal
  5. Mouse Nos. 21 to 25—ovalbumin 25 micrograms per animal+adjuvant 1 microgram per animal
  6. Mouse Nos. 26 to 30—ovalbumin 25 micrograms per animal+adjuvant 10 micrograms per animal
Second Immunization:
  The same set 21 days after first immunization by injection of 12.5 micrograms of ovalbumin/mouse to mouse nos. 6 to 30.
Third Immunization:
  The same set 35 days after first immunization by injection of 12.5 microgram of ovalbumin/mouse to mouse nos. 6 to 30.
  On day 42, blood samples from each mouse were collected. The stimulation index of each group was compared. The stimulation index was calculated by dividing the test pooled sera dilution yielding OD=1 by the dilution of pooled sera from mice immunized without the adjuvant, yielding OD=1. The results are shown in Table 6.

Example 8

Adjuvant activities of cyclo-L-Ala-L-Glu-(L-Trp-OH) (Compound 17), cyclo [L-Lys(Palmitoyil)-L-Glu(D-Trp-OH)] (Compound 26a), cyclo [D-Lys(Palmitoyil)-D-Glu(D-Trp-OH)] (Compound 26b), cyclo-L-Lys(N-acetyl-Glycosamine-N-acetyl-muramil)-L-Glu-(L-Trp-OH) (Compound 33a), and cyclo-D-Lys(N-acetyl-Glycosamine-N-acetyl-muramil)-D-Glu-(L-Trp-OH) (Compound 33b).
Stage 1:
  Adjuvant activity was tested on 11 groups of Balb/c mice (obtained from Stolbovaya Breeding Station). Each group consisted of 7 animals. Three immunizations were performed as follows:
First Immunization:
  Group 1—ovalbumin 25 micrograms per animal (Mouse Nos. 1 to 7)
  Group 2—ovalbumin 25 micrograms per animal+CFA (Complete Freund's adjuvant) (Mouse Nos. 8 to 14)
  Group 3—ovalbumin 25 micrograms per animal+adjuvant of compound 33a 100 micrograms per animal (Mouse Nos. 15 to 21)

Group 4—ovalbumin 25 micrograms per animal+adjuvant of compound 33a 10 micrograms per animal (Mouse Nos. 22 to 27)

Group 5—ovalbumin 25 micrograms per animal+adjuvant of compound 33a 1 microgram per animal (Mouse Nos. 28 to 35)

Group 6—ovalbumin 25 micrograms per animal+adjuvant of compound 33b 100 micrograms per animal (No. 36 to 42)

Group 7—ovalbumin 25 micrograms per animal+adjuvant of compound 33b 10 micrograms per animal (Mouse Nos. 43 to 49)

Group 8—ovalbumin 25 micrograms per animal+adjuvant of compound 33b 1 microgram per animal (Mouse Nos. 50 to 56)

Group 9—ovalbumin 25 micrograms per animal+adjuvant of compound 17 100 micrograms per animal (Mouse Nos. 57 to 63)

Group 10—ovalbumin 25 micrograms per animal+adjuvant of compound 17 10 micrograms per animal (Mouse Nos. 64 to 70)

Group 11—ovalbumin 25 micrograms per animal+adjuvant of compound 17 1 microgram per animal (Mouse Nos. 71 to 77)

Second Immunization:

The same set 14 days after first immunization by injection of 12.5 micrograms of ovalbumin/mouse to mouse nos. 1 to 77.

Third Immunization:

The same set 28 days after first immunization by injection of 12.5 micrograms of ovalbumin/mouse to mouse nos. 1 to 77.

On day 35 after first immunization, blood samples from each mouse were collected.

Figure 2:
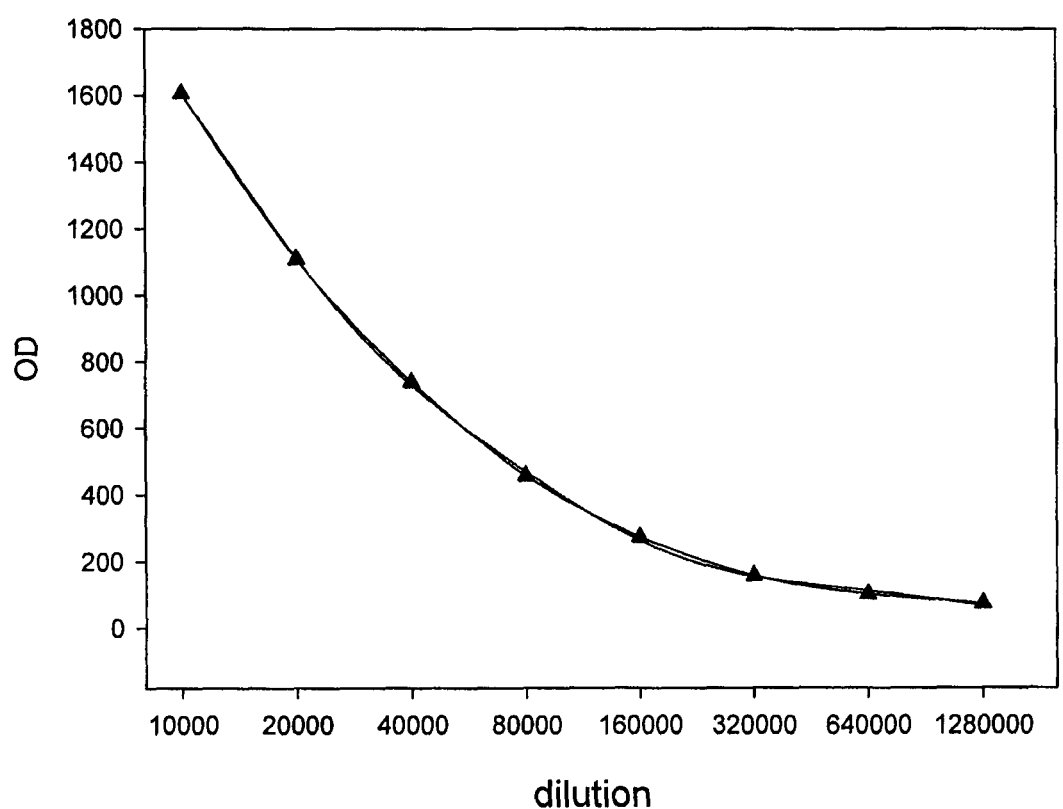
FIG. 2 shows the titration dilution graph of OVA+CFA.
Figure 3:
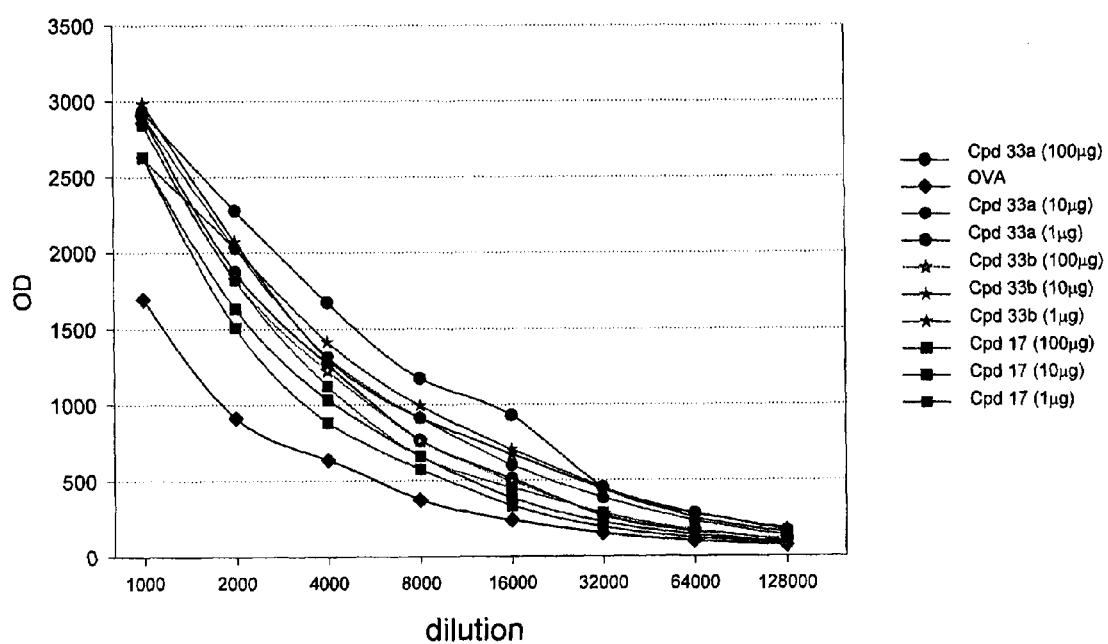
FIG. 3 shows the titration dilution graph of compounds 33a, 33b, 17 and OVA.

Enzyme-Linked Immunosorbent Assay (ELISA):

OVA (10 micrograms/ml) solution in 0.05 M sodium carbonate buffer (pH 9.5) was added to plate wells, 0.1 ml per well and incubated at 4° C. for 16 hours. The OVA solution was then removed and the plate was washed 4 times with PBS containing 0.05% Tween-20. Such washing was performed after each incubation stage. Serial twofold dilutions of sera (starting from 1:100 or 1:1000) were added to the wells, 0.1 ml per well and incubated at 37° C. for 1 hour followed by incubation (1 hour, 37° C.) with HRP-conjugated goat anti-mouse IgG antibodies (0.1 ml, 1 mg/ml in PBS) and then with a 0.1 mL substrate solution –0.05% $H_2O_2$ and 0.05% o-phenylene diamine in 0.05M sodium citrate buffer with a pH of 4.5. The reaction was stopped by adding 100 μl of 12.5% $H_2SO_4$. Absorbance was measured at a wavelength of 492 nm using a Multiscan Plus MKII (Flow Laboratories, Great Britain). Significant anti-protein antibody titer (for individual sera) was assessed as the serum dilution produced an absorbance value of more than 0.1 ODU and the minimum exceeds three times the control level. The antibody titer was presented and –log of dilution (FIGS. 2 and 3). The stimulation index for pooled sera was calculated by dividing the test pooled sera dilution producing OD=1 by the dilution of pooled sera from mice immunized without the adjuvant, producing OD=1. The results of the adjuvant activities of cyclo-L-Ala-L-Glu-(L-Trp-OH) (Compound 17), cyclo-L-Lys(N-acetyl-Glycosamine-N-acetyl-muramil)-L-Glu-(L-Trp-OH) (Compound 33a) and cyclo-D-Lys(N-acetyl-Glycosamine-N-acetyl-muramil)-D-Glu-(L-Trp-OH) (Compound 33b) are shown in Table 7 and the adjuvant activities of cyclo [L-Lys (Palmitoyil)-L-Glu(D-Trp-OH)] (Compound 26a) and cyclo [D-Lys(Palmitoyil)-D-Glu(D-Trp-OH)] (Compound 26b) are shown in Table 8 as well as in FIG. 4 which includes the results of the adjuvant activities of cyclo-L-Lys-L-Glu-(L-Trp-OH) (compound 19). It is noted that the peptides of compounds 26a and 26b are soluble in 0.1% $NH_4OH$ at a concentration of 1 mg per 1 to 2 ml. The peptides remain soluble when titrated with 0.1% AcOH to pH=8.4 to 8.5. As can bee seen from the results of the adjuvant activities of the compounds in FIG. 4, compound 17 is active at 1, 10 and 100 μg/kg; compound 19 is active at 100 μg/kg; compound 33a is active at 100 μg/kg; compound 33b is not an active compound, compound 26a is active at 10 μg/kg; and compound 26b is not an active compound.

Example 9

Studies on New Dermorphin Analogues (i) Evaluation of Peripheral Opioid Activity Peripheral opioid activity of the peptides was assessed on the basis of the ability to inhibit the electrically-induced contractions of isolated guinea pig ileum (GPI) (Kosterlitz, H. W. et al., "The effect of adrenaline, noradrenaline and isoprenaline on inhibition a- and b-adrenoreceptors in the longitudinal muscle of the guinea pig ileum", Brit. J. Pharmacol., Vol. 39., Pages 398 to 413, 1970).

The segment of GPI about 1 cm long was placed into a 10-ml organ bath containing Krebs solution at 34° C. The composition of the Krebs solution was (mM): NaCl—118; KCl—4.70; $CaCl_2$—2.52; $KH_2PO_4$—0.93; $MgSO_4$—1.27; $NaHCO_3$—25; glucose—11.0. Resting tension of the organ was 1 g. The segment of GPI was stimulated by single pulses duration 1 ms with 0.1 Hz at 80 V. The solution with isolated organs was constantly aerated. The contractions were recorded in an isometrical mode by a sensor K 30 (Hugo Sachs Elektronic KG) with paper register Rikadenki-series (Japan).

The substances tested were dissolved in distilled water and added cumulatively to the organ bath at a volume of 5 to 30 mcl. Each subsequent substance was added after the isolated organs were washed 3 or 4 times for 12-15 min. On the basis of the data obtained, dose-effects curves were plotted and the activity of substances was expressed by $IC_{50}$ or $pD_2$. The $pD_2$ index was equal to a negative decimal logarithm of the substance concentration causing a 50% of the maximal effect.

Statistical treatment of the results was carried out by the Student's t-test.

New dermorphin analogues were tested in the standard model of Guinea pig ileum binding test. For each molecule, the $EC_{50}$ was determined as concentration of substance causing the reduction of contraction amplitude by the 50% from basic level.

The standard preparation in all experiments was dermorphin. For confirmation of opioid activity, the specific antagonist naloxson was used in concentration of $10^{-5}$M. Each molecule was tested in 5 independent replications and relative activity was calculated as negative logarithm of $EC_{50}$ ($pD_2$).

As can be seen in Table 9, all tested peptides have different levels of opioid activities, in the range of $10^{-9}$ to $10^{-5}$ M, with the exception of H-Tyr-Tyr-Pro-Ser-$NH_2$ (Compound 51) and D-Ala-D-Glu-(D-Trp)-OH (Compound 54).

(ii) Analgesic Activity of New Opioid Peptide Analogues.

Two hundred and twenty mice F1(CBAxC57D16) first generation hybrids were used for testing of analgesic activity using the "tail flick" test. The water temperature was at 48° C. The maximal effect was for the period of 30 seconds. All peptides were injected intraperitoneally in the doses of 5, 10 or 20 mg/kg. Analgesic effect was estimated in the time interval of 15 to 120 min after peptide injection. Student's t-criterion was used for statistical calculations of the results. Statistical significance were at the level of p≤0.05. The results of the tests are shown in Table 10.

(iii) Analgesic Activity of Dermorphin and Analogues after Oral Administration and Intraperitoneal Administration.

For estimation of oral activity of novel cyclopeptides of the present invention, the "tail flick" test was used. The results were compared with those obtained using intraperitoneal administration.

Antinociceptive activity of the peptides of the present invention was assessed in experiments on BALB/c male mice weighing 22 to 24 g. The peptides were dissolved in saline and administered intraperitoneally or intragastrally.

The "Tail flick" test (D'Amour, F. E. et al. "A Method for Determining Loss of Pain Sensation", J. Pharmacol. Exp. Ther., Vol. 72, Pages 74 to 79, 1941) was performed on an analgesimeter type 812, Hugo Sachs Electronick KG. Antinociceptive activity was defined as the absence of tail flick response on stimulation with a focused bundle of heat radiation with 6 sec at baseline response of 2.0-3.0 seconds.

Statistical treatment of the results was carried out by the Student's paired t-test. The results of these testing are shown in Tables 11 and 12. As can be seen from the experiments, only cycloanalogues on neuropeptides are active in oral (intragastrally) administration.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Examples of multifunctional bioactive compounds and pharmaceutically acceptable salts, solvates and prodrugs thereof of the present invention.

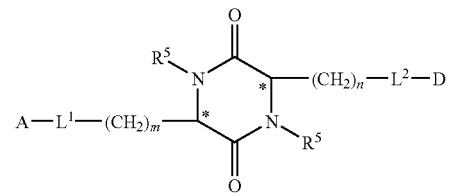

| Cpd | A | $L^1$ | m | * | n | $L^2$ | D | $R^5$ |
|---|---|---|---|---|---|---|---|---|
| (a) Tested Immuno- and hemodepressants: | | | | | | | | |
| 1 | D-Trp-OMe | —CO— | 2 | D-D | 1 | bond | H | H |
| 2 | D-Trp-OH | —CO— | 2 | D-D | 1 | bond | H | H |
| 3 | D-Trp-OMe | —CO— | 2 | D-D | 1 | bond | Bz | H |
| 4 | D-Trp-OH | —CO— | 2 | D-D | 1 | bond | Bz | H |
| 5 | D-Trp-ONH$_2$ | —CO— | 2 | D-D | 1 | bond | Bz | H |
| 6 | D-Trp-OMe | —CO— | 2 | D-D | 1 | bond | Ph | H |
| 7 | D-Trp-OH | —CO— | 2 | D-D | 1 | bond | Ph | H |
| 8 | D-Trp-NH$_2$ | —CO— | 2 | D-D | 1 | bond | Ph | H |
| 9 | D-Trp-NH$_2$ | —CO— | 2 | D-D | 4 | bond | H$_2$N | H |
| 10 | L-Trp-OMe | —CO— | 2 | D-D | 1 | bond | H | H |
| 11 | L-Trp-OH | —CO— | 2 | D-D | 1 | bond | H | H |
| 12 | D-Trp-OMe | —CO— | 1 | D-D | 1 | bond | H | H |
| 13 | D-Trp-OH | —CO— | 1 | D-D | 1 | bond | H | H |
| 14 | L-Trp-OMe | —CO— | 1 | D-D | 1 | bond | H | H |
| 15 | L-Trp-OH | —CO— | 1 | D-D | 1 | bond | H | H |
| (b) Tested Immuno- and hemostimulants | | | | | | | | |
| 16 | L-Trp-OMe | —CO— | 2 | L-L | 1 | bond | H | H |
| 17 | L-Trp-OH | —CO— | 2 | L-L | 1 | bond | H | H |
| 18 | L-Trp-NH$_2$ | —CO— | 2 | L-L | 4 | bond | H$_2$N | H |
| 19 | L-Trp-OH | —CO— | 2 | L-L | 4 | bond | H$_2$N | H |
| 20 | L-Trp-OMe | —CO— | 2 | L-L | 4 | bond | H$_2$N | H |
| 21 | D-Trp-OMe | —CO— | 1 | L-L | 1 | bond | H | H |
| 22 | D-Trp-OH | —CO— | 1 | L-L | 1 | bond | H | H |
| 23 | L-Trp-OMe | —CO— | 1 | L-L | 1 | bond | H | H |
| 24 | L-Trp-OH | —CO— | 1 | L-L | 1 | bond | H | H |
| (c) Tested Adjuvants | | | | | | | | |
| 25 | L-Trp-OMe | —CO— | 2 | L-L | 4 | —NH— | Palm* | H |
| 26a | L-Trp-OH | —CO— | 2 | L-L | 4 | —NH— | Palm | H |
| 26b | L-Trp-OH | —CO— | 2 | D-D | 4 | —NH— | Palm | H |
| 27 | L-Trp-NH$_2$ | —CO— | 2 | L-L | 4 | —NH— | Palm | H |
| 28 | D-Trp-OMe | —CO— | 1 | L-L | 4 | —NH— | Palm | H |
| 29 | D-Trp-OH | —CO— | 1 | L-L | 4 | —NH— | Palm | H |
| 30 | L-Trp-OMe | —CO— | 1 | L-L | 4 | —NH— | Palm | H |
| 31 | L-Trp-OH | —CO— | 1 | L-L | 4 | —NH— | Palm | H |

TABLE 1-continued

Examples of multifunctional bioactive compounds and pharmaceutically acceptable salts, solvates and prodrugs thereof of the present invention.

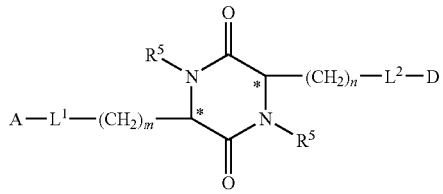

| Cpd | A | $L^1$ | m | * | n | $L^2$ | D | $R^5$ |
|---|---|---|---|---|---|---|---|---|
| 32 | L-Trp-$NH_2$ | —CO— | 2 | L-L | 4 | —NH— | N-Acetyl-Glucosamine (1-4)-N-Acetyl-muramic acid- | H |
| 33a | L-Trp-OH | —CO— | 2 | L-L | 4 | —NH— | N-Acetyl-Glucosamine (1-4)-N-Acetyl-muramic acid- | H |
| 33b | L-Trp-OH | —CO— | 2 | D-D | 4 | —NH— | N-Acetyl-Glucosamine (1-4)-N-Acetyl-muramic acid- | H |
| (d) Peptide analgesics + immunoactive derivatives | | | | | | | | |
| 34 | D-Trp-OMe | —CO— | 2 | D-D | 4 | —NH— | Tyr-D-Ala-Phe-D-Ala-Tyr-Pro-Ser- | H |
| 35 | D-Trp-OH | —CO— | 2 | D-D | 4 | —NH— | Tyr-D-Ala-Phe-D-Ala-Tyr-Pro-Ser- | H |
| 36 | D-Trp-$NH_2$ | —CO— | 2 | D-D | 4 | —NH— | Tyr-D-Ala-Phe-D-Ala-Tyr-Pro-Ser- | H |
| 37 | L-Trp-OMe | —CO— | 2 | L-L | 4 | —NH— | Tyr-D-Ala-Phe-D-Ala-Tyr-Pro-Ser- | H |
| 38 | L-Trp-OH | —CO— | 2 | L-L | 4 | —NH— | Tyr-D-Ala-Phe-D-Ala-Tyr-Pro-Ser- | H |
| 39 | L-Trp-$NH_2$ | —CO— | 2 | L-L | 4 | —NH— | Tyr-D-Ala-Phe-D-Ala-Tyr-Pro-Ser- | H |
| 40 | D-Trp-OMe | —CO— | 1 | D-D | 4 | —NH— | Tyr-D-Ala-Phe-D-Ala-Tyr-Pro-Ser- | H |
| 41 | D-Trp-OH | —CO— | 1 | D-D | 4 | —NH— | Tyr-D-Ala-Pbe-D-Ala-Tyr-Pro-Ser- | H |
| 42 | L-Trp-OMe | —CO— | 1 | D-D | 4 | —NH— | Tyr-D-Ala-Phe-D-Ala-Tyr-Pro-Ser- | H |
| 43 | L-Trp-OH | —CO— | 1 | D-D | 4 | —NH— | Tyr-D-Ala-Phe-D-Ala-Tyr-Pro-Ser- | H |

*Palm = Palmitoyl (hexadecanoyl)

TABLE 2

Spleen colony formation by bone marrow cells of novel peptides-treated mice.

| Donor treatment and method of introduction | Colony count CFU-8 - S per $10^5$ cells M ± M | % suppression |
|---|---|---|
| Control | 11.2 ± 0.4 | — |
| cyclo-DAla-DGlu-(DTrp-ONa) (i/p) | 5.0 ± 0.3* | 70 |
| cyclo-DAla-DGlu-(DTrp-ONa) (per os) | 6.0 ± 0.7* | 58 |
| cyclo-DAla-DGlu-(DTrp-OMe) (s/c) | 6.8 ± 0.4* | 47 |
| cyclo-DAla-DGlu-(DTrp-OMe) (per os) | 7.4 ± 0.4* | 40 |
| cyclo-LAla-LGlu-(LTrp-ONa) (i/p) | 11.7 ± 0.8 | 0 |
| cyclo-LAla-LGlu-(DTrp-ONa) (i/p) | 8.8 ± 0.2* | 20 |
| cyclo-DAla-DAsp-(DTrp-OH) (per/os) | 9.0 ± 0.2 | 26.5 |
| cyclo-DPhe-DGlu-(DTrp-ONa) (per os) | 8.1 ± 0.4* | 28 |
| cyclo-DTyr-DGlu-(DTrp-OH) (per os) | 6.3 ± 0.9* | 44 |
| γDGlu-DTrp (Thymodepressin) (i/p) | 6.3 ± 0.6* | 55 |

*P < 0.05 compare to control

TABLE 3

Comparison of the activities of novel compounds of the invention and thymodepressin on the suppression of CFU-S population in the bone marrow.

| Substance (Dose - microgram/per mouse) | Colony count CFU-8 - S per $10^5$ cells M ± m | % suppression |
|---|---|---|
| control | 9.9 ± 0.7 | — |
| γDGlu-DTrp (Thymodepressin) 200.0 (per os) | 5.1 ± 0.2* | 52 |
| γDGlu-DTrp (Thymodepressin) 20.0 (per os) | 6.4 ± 0.5* | 41 |
| γDGlu-DTrp (Thymodepressin) 2.0 (per os) | 8.0 ± 0.5 | 33 |
| γDGlu-DTrp (Thymodepressin) 0.2 (per os) | 10.2 ± 0.3 | 0 |
| γDGlu-DTrp (Thymodepressin) 0.2 (i/p) | 5.7 ± 0.4* | 51 |
| cyclo-DAla-DGlu-(DTrp-ONa) 0.2 (per os) | 5.3 ± 0.6* | 59 |
| cyclo-DAla-DGlu-(DTrp-OMe) 0.2 (per os) | 6.5 ± 0.5* | 42 |
| cyclo-DAla-DAsp-(DTrp-OMe) 0.2 (per/os) | 8.4 ± 0.6* | 28 |
| cyclo-DAla-DAsp-(DTrp-ONa) 0.2 (per/os) | 6.8 ± 0.8* | 55 |
| cyclo-DPhe-DGlu-(DTrp-ONa) 0.2 (per os) | 8.1 ± 0.4* | 28 |
| cyclo-DTyr-DGlu-(DTrp-ONa) 0.2 (per os) | 6.3 ± 0.9* | 44 |

*P < 0.05 compare to control

TABLE 4

Effect of Neogen or novel cyclic peptides of the invention on the formation of exogenous spleen colonies by irradiating bone marrow in vitro with 1 Gy.

| Radiation Dose | Peptide | Peptide dose, µg/kg | Route of administration | Colony count | % stimulation |
|---|---|---|---|---|---|
| — | — | — | — | 11.9 ± 0.4 | 100 |
| 1 Gy | — | — | — | 6.2 ± 0.6** | 0 |
| 1 Gy | Neogen | 10 | IP | 9.7 ± 0.4* | 81.5 |
| 1 Gy | Neogen | 100 | IP | 9.2 ± 0.7* | 77.3 |
| 1 Gy | Neogen | 10 | IM | 11.6 ± 0.8* | 97.5 |
| 1 Gy | Neogen | 100 | IM | 11.8 ± 0.9* | 99.1 |
| 1 Gy | Neogen | 100 | per/os | 6.7 ± 0.5 | 0 |
| 1 Gy | Neogen | 1000 | per/os | 6.1 ± 0.3 | 0 |
| 1 Gy | Cyclo-LAla-LGlu-(LTrp-ONa) | 100 | IP | 9.6 ± 0.7* | 80.7 |
| 1 Gy | Cyclo-LAla-LGlu-(LTrp-ONa) | 10 | IP | 8.0 ± 0.4* | 67.2 |
| 1 Gy | Cyclo-LAla-LGlu-(LTrp-ONa) | 100 | per/os | 11.7 ± 0.6* | 98.3 |
| 1 Gy | Cyclo-LAla-LGlu-(LTrp-OMe) | 100 | per/os | 8.9 ± 0.5* | 74.8 |
| 1 Gy | Cyclo-LAla-LGlu-(LTrp-OMe) | 100 | s/c | 8.0 ± 0.5* | 67.2 |

**Significance was calculated relative to this group
*P < 0.05

TABLE 5

Adjuvant activity of cyclo-L-Ala-L-Glu-(L-Trp-ONa).

| Tested product | Stimulation index |
|---|---|
| CFA (group 1) | — |
| Control (group 2) | 1.00 |
| Group with CFA + ovalbumin (25 microgram/mouth) (group 3) | 2.40 |
| Cyclo-L-Ala-L-Glu-(L-Trp-ONa) 1 µg/mouse (group 4) | 1.18 |
| Cyclo-L-Ala-L-Glu-(L-Trp-ONa) 10 µg/mouse (group 5) | 1.74 |

TABLE 6

Adjuvant activity of cyclo-L-Ala-L-Glu-(L-Trp-OH) (Compound 17).

| Adjuvant | Stimulation index |
|---|---|
| Compound 17 at 100 micrograms | 1.14 |
| Compound 17 at 10 micrograms | 1.74 |
| Compound 17 at 1 micrograms | 1.18 |
| Complete Freund's Adjuvant | 2.40 |
| Mouse Nos. 6 to 20 - ovalbumin 25 micrograms per animal | 1.0 |

TABLE 7

Anti-OVA antibody titers following protein-adjuvant immunizations and corresponding stimulation indices.

| Immunogen | Adjuvant | Dose, µg per animal | Anti-protein antibody titer (for individual sera) | | | | | | | Anti-protein antibody titer (pooled sera) | Stimulation index |
|---|---|---|---|---|---|---|---|---|---|---|---|
| OVA | Cpd 33a | 100 | 4.8 | 4.8 | 5.4 | 5.1 | 6.4 | 5.1 | 5.7 | 5.5 | 6.8 |
| | | 10 | 4.4 | 5.7 | 4.7 | 5.7 | 5.7 | 5.7 | 5.4 | 5.1 | 3.5 |
| | | 1 | 5.1 | 4.2 | 5.4 | 4.1 | 5.1 | 5.4 | 5.4 | 4.8 | 2.9 |
| | Cpd 33b | 100 | 4.8 | 5.4 | 4.2 | 5.1 | 5.1 | 5.4 | 5.4 | 4.8 | 2.9 |
| | | 10 | 4.8 | 4.5 | 5.2 | 5.1 | 5.4 | 4.3 | 5.4 | 5.4 | 4.1 |
| | | 1 | 5.2 | 4.8 | 4.8 | 4.8 | 4.5 | 5.1 | 4.8 | 5.1 | 3.5 |
| | Cpd 17 | 100 | 4.5 | 4.2 | 4.2 | 4.2 | 5.1 | 5.1 | 4.8 | 4.8 | 2.3 |
| | | 10 | 4.8 | 4.2 | 4.1 | 4.5 | 5.4 | 4.5 | 3.9 | 4.5 | 1.9 |
| | | 1 | 5.1 | 4.2 | 4.5 | 5.1 | 5.4 | 5.1 | 4.5 | 4.8 | 2.6 |
| | CFA | | 5.3 | 6.8 | 6.2 | 5.3 | 6.2 | 6.8 | 5.9 | 6.2 | 13 |
| | None | | 4.2 | 4.5 | 4.2 | 4.5 | 4.8 | 4.5 | 3.9 | 4.5 | 1 |

TABLE 8

Stimulation Indices for adjuvants compounds 26a and 26b.

| Immunogen | Adjuvant | Dose, µg per animal | Anti-protein antibody titer | | | | | | | Pool | Stimulation index |
|---|---|---|---|---|---|---|---|---|---|---|---|
| | | | 15 | 16 | 17 | 18 | 19 | 20 | 21 | | |
| OVA | Cpd 26b | 100 | 4.5 | 4.5 | 4.8 | 4.8 | 4.2 | 4.8 | | 4.8 | 2.6 |

TABLE 8-continued

Stimulation Indices for adjuvants compounds 26a and 26b.

| Immunogen | Adjuvant | Dose, μg per animal | Anti-protein antibody titer | | | | | | | Pool | Stimulation index |
|---|---|---|---|---|---|---|---|---|---|---|---|
| | | 10 | *29* 4.7 | *30* 5.1 | *31* 4.7 | *32* 4.8 | *33* 4.7 | *34* — | *35* 4.8 | 4.8 | 2.7 |
| | | 1 | *36* 5.4 | *37* 4.5 | *38* 3.8 | *39* 3.5 | *40* 5.1 | *41* 5.4 | | 5.1 | 4.9 |
| | Cpd 26a | 100 | *22* 4.8 | *23* 4.4 | *24* 4.8 | *25* 5.1 | *26* 4.8 | *27* 4.8 | *28* 5.4 | 5.1 | 3.3 |
| | | 10 | *42* 5.5 | *43* 5.5 | *44* 5.8 | *45* 5.5 | *46* 5.7 | *47* 5.7 | *48* 5.5 | 5.7 | 6.5 |
| | | 1 | *49* 4.8 | *50* 5.1 | *51* 4.5 | *52* 4.4 | *53* 5.1 | *54* 5.1 | *55* 5.1 | 4.4 | 2.0 |
| | CFA | | *8* 6.2 | *9* 5.9 | *10* 6.2 | *11* 6.2 | *12* 6.2 | *13* 6.2 | *14* 5.9 | 6.2 | 18 |
| | None | | *1* 4.1 | *2* 4.2 | *3* 4.2 | *4* 3.9 | *5* 4.5 | *6* 3.9 | *7* 3.5 | 3.9 | 1 |

TABLE 9

In vitro (GPI - μ-receptor binding activity) test results of the peripheral opioid activity of peptides.

| Cpd | Dermorphin Analogues | Median $EC_{50}$ in M | Value of $pD_2$ (M ± m) | Antagonism with naloxon $10^{-5}$ M |
|---|---|---|---|---|
| 44 | Cyclo-[L-Lys(H-Tyr-D-Ala-Phe-D-Ala)-L-Glu(OH)] | $5.7 \times 10^{-7}$ | 6.15 ± 0.10 | + |
| 45 | Cyclo-[L-Lys(H-Tyr-D-Ala-Phe-D-Ala)-L-Glu(L-Trp-OMe)] | $2 \times 10^{-6}$ | 5.68 ± 0.09 | + |
| 46 | Cyclo-[L-Lys(H-Tyr-D-Ala-Phe-D-Ala-Tyr-Pro-Ser)-L-Glu(L-Trp-NH$_2$)] | $1.1 \times 10^{-8}$ | 7.96 ± 0.02 | + |
| 47 | Cyclo-[L-Lys(H-Tyr-D-Ala-Phe-D-Ala-Tyr-Pro-Ser)-L-Glu(L-Trp-OH)] | $3.3 \times 10^{-8}$ | 7.52 ± 0.07 | + |
| 48 | (Dermorphin) H-Tyr-D-Ala-Phe-Gly-Tyr-Pro-Ser-NH$_2$ | $2.5 \times 10^{-9}$ | 8.56 ± 0.12 | + |
| 49 | H-Tyr-D-Ala-Phe-D-Ala-Tyr-Pro-Ser-NH$_2$ | $3 \times 10^{-8}$ | 7.55 ± 0.11 | + |
| 50 | H-Tyr-D-Ala-Phe-D-Ala-Tyr-Pro-Ser-NH-CH$_3$ | $9.5 \times 10^{-9}$ | 7.95 ± 0.07 | + |
| 51 | H-Tyr-Tyr-Pro-Ser-NH$_2$ | — | — | — |
| 52 | Arg-Tyr-D-Ala-Phe-Gly-OH | $3 \times 10^{-6}$ | 5.50 ± 0.07 | + |
| 53 | H-Arg-Tyr-D-Ala-Phe-D-AlaOH | $1 \times 10^{-6}$ | 6.06 ± 0.12 | + |
| 54 | D-Ala-D-Glu-(D-Trp)-OH | — | — | — |
| 55 | H-Tyr-D-Ala-Phe-Gly-OH | $1 \times 10^{-6}$ | 5.81 ± 0.16 | + |
| 56 | H-Tyr-D-Ala-Gly-Phe-Leu-Arg-OH | $5 \times 10^{-8}$ ($1 \times 10^{-8}$) | 7.53 ± 0.22 | + |

TABLE 10

Analgesic activity of opioid peptide analogues.

| Structure | Dose (mg/kg) | Mice No. | Initial sensitivity level (sec.) | Time after peptide injection (min.) | | | | | |
|---|---|---|---|---|---|---|---|---|---|
| | | | | 15 | 30 | 45 | 60 | 90 | 120 |
| | | | | Effect duration (sec.) | | | | | |
| Dermorphin: Tyr-DAla-Phe-Gly-Tyr-Pro-Ser-NH$_2$ | 5 | 8 | 3.6 ± 0.2 | 11.0 ± 1.0 | 14.4 ± 3.0 | 17.2 ± 2.4 | 13.2 ± 3.2 | 4.7 ± 0.3 | — |
| | 10 | 10 | 4.4 ± 0.3 | 11.7 ± 1.0 | 16.6 ± 2.2 | 17.0 ± 2.3 | 10.2 ± 1.2 | 3.9 ± 0.2 | — |
| Opilong: Tyr-DAla-Phe-DAla-Tyr-Pro-Ser-NHMe | 5 | 10 | 3.0 ± 0.1 | 9.0 ± 1.7 | 10.3 ± 2.6 | 14.3 ± 3.7 | 10.8 ± 1.9 | 6.4 ± 1.5 | 3.5 ± 0.2 |
| | 10 | 10 | 2.9 ± 0.2 | 5.9 ± 0.7 | 10.7 ± 0.8 | 12.2 ± 2.6 | 7.2 ± 1.2 | 6.9 ± 1.4 | 3.7 ± 0.4 |
| Cyclo-[L-Lys(H-Tyr-D-Ala-Phe-D-Ala-Tyr-Pro-Ser)-L-Glu(L-Trp-OH)] | 10 | 15 | 3.7 ± 0.2 | 6.8 ± 0.6 | 6.3 ± 0.7 | 8.4 ± 1.4 | 7.7 ± 1.7 | 6.7 ± 1.0 | 4.6 ± 0.3 |
| | 20 | 10 | 3.4 ± 0.2 | 7.8 ± 0.5 | 8.3 ± 0.8 | 8.7 ± 1.2 | 9.5 ± 1.2 | 9.7 ± 1.3 | 8.2 ± 1.7 |

TABLE 10-continued

Analgesic activity of opioid peptide analogues.

| Structure | Dose (mg/kg) | Mice No. | Initial sensitivity level (sec.) | 15 | 30 | 45 | 60 | 90 | 120 |
|---|---|---|---|---|---|---|---|---|---|
| | | | | | Time after peptide injection (min.) | | | | |
| | | | | | Effect duration (sec.) | | | | |
| Cyclo-[L-Lys(H-Tyr-D-Ala-Phe-D-Ala-Tyr-Pro-Ser)-L-Glu(L-Trp-NH$_2$)] | 10 | 10 | 3.2 ± 0.3 | 11.6 ± 1.7 | 15.5 ± 1.6 | 15.7 ± 1.2 | 13.0 ± 1.5 | 9.9 ± 1.5 | 6.8 ± 0.5 |
| | 20 | 10 | 3.0 ± 0.2 | 1.4 ± 1.6 | 18.1 ± 2.3 | 16.8 ± 2.2 | 12.7 ± 1.8 | 11.7 ± 1.2 | 6.3 ± 0.6 |

Statistically significant data (p ≤ 0.05) shown in bold.

TABLE 11

Analgesic activity of Dermorphin and analogues after oral administration as determined from the "tail flick" test.

| Structure | Dose (mg/kg) | Mice No. | Initial sensitivity level, mean (sec.) | 15 | 30 | 60 | 90 | 120 |
|---|---|---|---|---|---|---|---|---|
| | | | | | Time after peptide injection (min.) | | | |
| | | | | | Effect duration (sec.) | | | |
| Tyr-DAla-Phe-Gly-Tyr-Pro-Ser-NH$_2$ Dermorphin | 50 | 6 | 2.2 ± 0.1 | 2.4 ± 0.1 | 2.3 ± 0.1 | 2.3 ± 0.1 | 3.4 ± 0.5 | |
| Tyr-DAla-Phe-DAla-Tyr-Pro-Ser-NHMe Opilong | 50 | 7 | 2.6 ± 0.1 | 3.3 ± 0.6 | 2.3 ± 0.1 | — | 4.3 ± 0.6 | |
| Cyclo-[L-Lys(H-Tyr-D-Ala-Phe-D-Ala-Tyr-Pro-Ser)-L-Glu(L-Trp-OH)] | 50 | 8 | 2.2 ± 0.1 | **3.7* ± 0.5** | **3.9* ± 0.5** | **4.1* ± 0.5** | **4.0* ± 0.5** | — |
| Cyclo-[L-Lys(H-Tyr-D-Ala-Phe-D-Ala-Tyr-Pro-Ser)-L-Glu(L-Trp-NH$_2$)] | 50 | 6 | 2.7 ± 0.1 | **4.5* ± 0.1** | **4.1* ± 0.5** | **5.5* ± 0.5** | **5.5* ± 0.4** | **5.5* ± 0.5** |
| Tramadol | 50 | 6 | 2.6 ± 0.1 | 2.6 ± 0.1 | **4.6* ± 0.5** | **4.4* ± 0.5** | **4.4* ± 0.6** | **4.4* ± 0.5** |

Statistically significant data (p ≤ 0.05) shown in bold.

TABLE 12

Analgesic activity of Dermorphin and analogues after intraperitoneal administration.

| Molecule | Dose (mg/kg) | Mice No. | Initial sensitivity level, mean (sec.) | 15 | 30 | 45 | 60 | 90 | 120 |
|---|---|---|---|---|---|---|---|---|---|
| | | | | | Time after peptide injection (min.) | | | | |
| | | | | | Effect duration (sec.) | | | | |
| Tyr-DAla-Phe-Gly-Tyr-Pro-Ser-NH$_2$ Dermorphin | 10 | 8 | 2.2 ± 0.2 | **5.6* ± 0.4** | **6.0* ± 0** | | | | |
| Tyr-DAla-Phe-DAla-Tyr-Pro-Ser-NHMe Opilong | 10 | 6 | 2.0 ± 0.1 | 3.6 ± 0.7 | **5.6* ± 0.4** | **5.5* ± 0.6** | **5.2* ± 0.6** | — | — |

TABLE 12-continued

Analgesic activity of Dermorphin and analogues after intraperitoneal administration.

| Molecule | Dose (mg/kg) | Mice No. | Initial sensitivity level, mean (sec.) | Time after peptide injection (min.) | | | | | |
|---|---|---|---|---|---|---|---|---|---|
| | | | | 15 | 30 | 45 | 60 | 90 | 120 |
| | | | | Effect duration (sec.) | | | | | |
| Cyclo-[L-Lys(H-Tyr-D-Ala-Phe-D-Ala-Tyr-Pro-Ser)-L-Glu(L-Trp-OH)] | 10 | 9 | 2.1 ± 0.1 | 4.1 ± 0.4 | **5.6* ± 0.4** | **4.8* ± 0.6** | — | — | — |
| Cyclo-[L-Lys(H-Tyr-D-Ala-Phe-D-Ala-Tyr-Pro-Ser)-L-Glu(L-Trp-NH$_2$)] | 10 | 5 | 2.1 ± 0.1 | 3.9 ± 0.8 | **5.3* ± 0.7** | **5.2* ± 0.6** | — | — | — |
| Arg-Tyr-DAla-Phe-DAla-OH | 10 | 9 | 2.4 ± 0.1 | 2.7 ± 0.1 | — | — | — | — | — |

Statistically significant data (p ≤ 0.05) shown in bold.

What is claimed is:

1. A compound of Formula I:

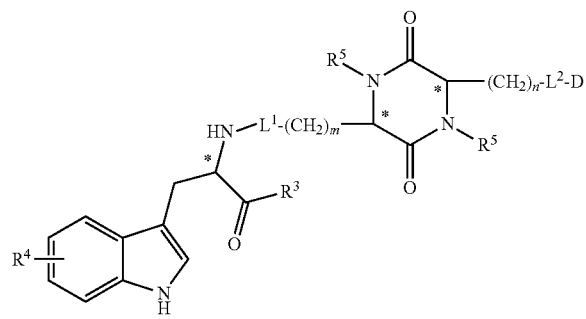

I wherein
$R^3$ is selected from the group consisting of H, OH, OC$_{1-6}$alkyl, NH$_2$, NHC$_{1-6}$alkyl, N(C$_{1-6}$alkyl)$_2$, NHNH$_2$ and OY, where Y is a cation selected from a lithium, sodium, potassium, calcium, magnesium, barium, zinc, aliphatic ammonium, aromatic ammonium and NH$_4^+$ cation;
$R^4$ is 1 to 4 substituents independently selected from the group consisting of H, halo, OH, OC$_{1-6}$alkoxy, C$_2$-C$_6$alkenyl, C$_2$-C$_6$alkenyloxy, NH$_2$, NH(C$_{1-6}$alkyl), N(C$_{1-6}$alkyl)(C$_{1-6}$alkyl), CN, CF$_3$, OCF$_3$, NO$_2$, C(O)C$_{1-6}$alkyl, C(O)OC$_{1-6}$alkyl, SO$_2$C$_{1-6}$alkyl, SO$_2$NH$_2$, SO$_2$NHC$_{1-6}$alkyl, phenyl and C$_{1-6}$alkylenephenyl;
$L^1$ and $L^2$ are each independently a linker group selected from the group consisting of a single bond, —C(O)—, —C(O)NR$^2$—, —NR$^2$C(O)—, —NR$^2$—, —C(O)O—, —OC(O)—, —S—S—, —SO$_2$NR$^2$—, —NR$^2$SO$_2$—, —S— and —O—;
$R^2$ is selected from the group consisting of H, C$_{1-6}$alkyl, C$_{1-6}$alkylenearyl, C(O)C$_{1-6}$alkyl, C(O)aryl, SO$_2$C$_{1-6}$alkyl and SO$_2$aryl;
$R^5$ is H or C$_{1-6}$alkyl;
* is the L or D configuration or mixtures thereof;
** is the L or D configuration or mixtures thereof;
m is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50;
n is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50; and
D is selected from the group consisting of H, C$_{1-6}$alkyl, a side chain of an amino acid, and a biologically active moiety;
or a pharmaceutically acceptable salt, or ester or amide prodrug thereof.

2. The compound according to claim 1, wherein each of $L^1$ and $L^2$ is independently selected from the group consisting of —C(O)—, —NR$^2$—, —C(O)NR$^2$— and —NR$^2$C(O)—.

3. The compound according to claim 2, wherein $R^2$ is selected from the group consisting of H, Me, Bn, C(O)Me, C(O)Ph, SO$_2$Me and SO$_2$Ph.

4. The compound according to claim 3, wherein $R^2$ is H.

5. The compound according to claim 1, wherein $R^4$ is a substituent selected from the group consisting of H, halo, OH, OMe, Me, vinyl, vinyloxy, NH$_2$, NHMe, NMe$_2$, CN, CF$_3$, OCF$_3$, NO$_2$, C(O)Me, C(O)OMe, SO$_2$Me, SO$_2$NH$_2$, SO$_2$NHMe, phenyl and benzyl.

6. The compound according to claim 5, wherein $R^4$ is H.

7. The compound according to claim 1, wherein $R^3$ is selected from the group consisting of H, OH, OMe, NH$_2$, NHMe, NMe$_2$, NHNH$_2$ and OY.

8. The compound according to claim 1, wherein Y is selected from the group consisting of Na$^+$, K$^+$ and Zn$^{2+}$.

9. The compound according to claim 1, wherein m is 1, 2, 3, 4, 5 or 6.

10. The compound according to claim 1, wherein n is 0, 1, 2, 3, 4, 5, 6, 7, 8, 9 or 10.

11. The compound according to claim 1, wherein $R^5$ is H or Me.

12. The compound according to claim 1, wherein both * in the diketopiperazine ring are in the D configuration or both * are in the L configuration.

13. The compound according to claim 1, wherein D is a biologically active moiety selected from the group consisting of adjuvants, analgesics, opiates, antidotes, synthetic vaccines, pharmaceutical pharmacophores, sugars, lipids and nucleotides.

14. A compound according to claim 1 having the following formula:

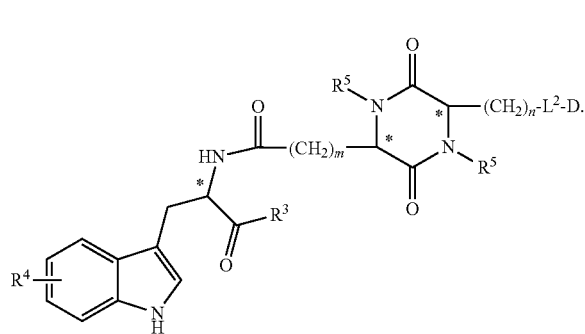

15. The compound according to claim 1, selected from the compounds listed below:

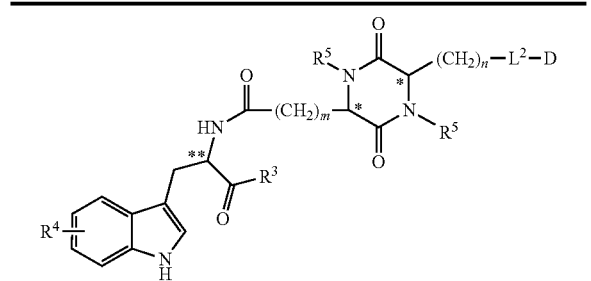

| Cpd | R³ | ** | m | * | N | L² | D | R⁵ |
|---|---|---|---|---|---|---|---|---|
| 1 | OMe | D | 2 | D-D | 1 | bond | H | H |
| 2 | OH | D | 2 | D-D | 1 | bond | H | H |
| 3 | OMe | D | 2 | D-D | 1 | bond | Bz | H |
| 4 | OH | D | 2 | D-D | 1 | bond | Bz | H |
| 5 | ONH₂ | D | 2 | D-D | 1 | bond | Bz | H |
| 6 | OMe | D | 2 | D-D | 1 | bond | Ph | H |
| 7 | OH | D | 2 | D-D | 1 | bond | Ph | H |
| 8 | NH₂ | D | 2 | D-D | 1 | bond | Ph | H |
| 9 | NH₂ | D | 2 | D-D | 4 | bond | H₂N | H |
| 10 | OMe | L | 2 | D-D | 1 | bond | H | H |
| 11 | OH | L | 2 | D-D | 1 | bond | H | H |
| 12 | OMe | D | 1 | D-D | 1 | bond | H | H |
| 13 | OH | D | 1 | D-D | 1 | bond | H | H |
| 14 | OMe | L | 1 | D-D | 1 | bond | H | H |
| 15 | OH | L | 1 | D-D | 1 | bond | H | H |
| 16 | OMe | L | 2 | L-L | 1 | bond | H | H |
| 17 | OH | L | 2 | L-L | 1 | bond | H | H |
| 18 | NH₂ | L | 2 | L-L | 4 | bond | H₂N | H |
| 19 | OH | L | 2 | L-L | 4 | bond | H₂N | H |
| 20 | OMe | L | 2 | L-L | 4 | bond | H₂N | H |
| 21 | OMe | D | 1 | L-L | 1 | bond | H | H |
| 22 | OH | D | 1 | L-L | 1 | bond | H | H |
| 23 | OMe | L | 1 | L-L | 1 | bond | H | H |
| 24 | OH | L | 1 | L-L | 1 | bond | H | H |
| 25 | OMe | L | 2 | L-L | 4 | —NH— | hexadecanoyl | H |
| 26a | OH | L | 2 | L-L | 4 | —NH— | hexadecanoyl | H |
| 26b | OH | L | 2 | D-D | 4 | —NH— | hexadecanoyl | H |
| 27 | NH₂ | L | 2 | L-L | 4 | —NH— | hexadecanoyl | H |
| 28 | OMe | D | 1 | L-L | 4 | —NH— | hexadecanoyl | H |

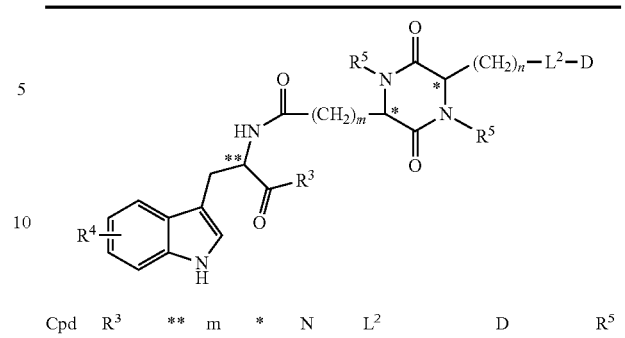

| Cpd | R³ | ** | m | * | N | L² | D | R⁵ |
|---|---|---|---|---|---|---|---|---|
| 29 | OH | D | 1 | L-L | 4 | —NH— | hexadecanoyl | H |
| 30 | OMe | L | 1 | L-L | 4 | —NH— | hexadecanoyl | H |
| 31 | OH | L | 1 | L-L | 4 | —NH— | hexadecanoyl | H |
| 32 | NH₂ | L | 2 | L-L | 4 | —NH— | N-Acetyl-Glucosamine (1-4)-N-Acetyl-muramic acid- | H |
| 33a | OH | L | 2 | L-L | 4 | —NH— | N-Acetyl-Glucosamine (1-4)-N-Acetyl-muramic acid- | H |
| 33b | OH | L | 2 | D-D | 4 | —NH— | N-Acetyl-Glucosamine (1-4)-N-Acetyl-muramic acid- | H |
| 34 | OMe | D | 2 | D-D | 4 | —NH— | Tyr-D-Ala-Phe-D-Ala-Tyr-Pro-Ser- | H |
| 35 | OH | D | 2 | D-D | 4 | —NH— | Tyr-D-Ala-Phe-D-Ala-Tyr-Pro-Ser- | H |
| 36 | NH₂ | D | 2 | D-D | 4 | —NH— | Tyr-D-Ala-Phe-D-Ala-Tyr-Pro-Ser- | H |
| 37 | OMe | L | 2 | L-L | 4 | —NH— | Tyr-D-Ala-Phe-D-Ala-Tyr-Pro-Ser- | H |
| 38 | OH | L | 2 | L-L | 4 | —NH— | Tyr-D-Ala-Phe-D-Ala-Tyr-Pro-Ser- | H |
| 39 | NH₂ | L | 2 | L-L | 4 | —NH— | Tyr-D-Ala-Phe-D-Ala-Tyr-Pro-Ser- | H |
| 40 | OMe | D | 1 | D-D | 4 | —NH— | Tyr-D-Ala-Phe-D-Ala-Tyr-Pro-Ser- | H |
| 41 | OH | D | 1 | D-D | 4 | —NH— | Tyr-D-Ala-Phe-D-Ala-Tyr-Pro-Ser- | H |
| 42 | OMe | L | 1 | D-D | 4 | —NH— | Tyr-D-Ala-Phe-D-Ala-Tyr-Pro-Ser- | H |
| 43 | OH | L | 1 | D-D | 4 | —NH— | Tyr-D-Ala-Phe-D-Ala-Tyr-Pro-Ser- | H |
| 45 | OMe | L | 2 | L-L | 4 | —NH— | H-Tyr-D-Ala-Phe-D-Ala | H. |

16. The compound according to claim 1, wherein the prodrug is an aliphatic ester, phenyl ester, acyloxymethyl ester, carbamate or an amino acid ester.

17. The compound of claim 1, wherein D is selected from the group consisting of palmitoyl, peptide analgesics, dermorphin, morphine, naloxone, antigenic determinants, T- and B-epitopes, methotrexate, diclofenac, ibuprofen, indomethacine, naproxen and ketoprofen.

18. A pharmaceutical composition comprising a compound according to claim 1 and a pharmaceutically acceptable carrier.

* * * * *

UNITED STATES PATENT AND TRADEMARK OFFICE
CERTIFICATE OF CORRECTION

PATENT NO. : 8,637,521 B2  
APPLICATION NO. : 12/376138  
DATED : January 28, 2014  
INVENTOR(S) : Vladislav I. Deigin Page 1 of 1

It is certified that error appears in the above-identified patent and that said Letters Patent is hereby corrected as shown below:

In the Claims

1. Column 33, lines 30-40, Claim 1, chemical Formula I should read:

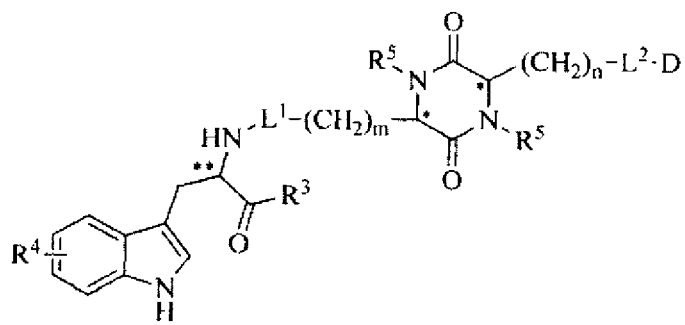

2. Column 35, lines 5-15, Claim 14, chemical Formula I should read:

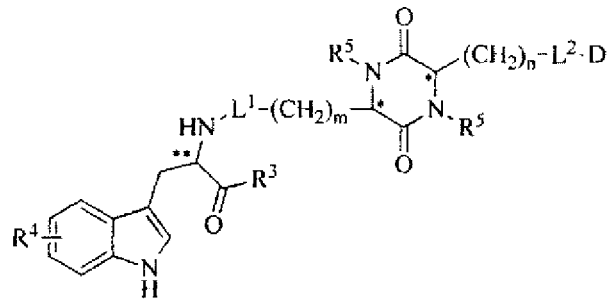

Signed and Sealed this  
Twenty-fourth Day of February, 2015

Michelle K. Lee  
*Deputy Director of the United States Patent and Trademark Office*

UNITED STATES PATENT AND TRADEMARK OFFICE
CERTIFICATE OF CORRECTION

PATENT NO.       : 8,637,521 B2
APPLICATION NO.  : 12/376138
DATED            : January 28, 2014
INVENTOR(S)      : Vladislav I. Deigin It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 562 days.

Signed and Sealed this
Twenty-second Day of September, 2015

Michelle K. Lee
*Director of the United States Patent and Trademark Office*